(12) United States Patent
Fish

(10) Patent No.: US 9,119,738 B2
(45) Date of Patent: Sep. 1, 2015

(54) METHOD AND APPARATUS FOR THE ENDOLUMINAL DELIVERY OF INTRAVASCULAR DEVICES

(75) Inventor: R. David Fish, Houston, TX (US)

(73) Assignee: COLIBRI HEART VALVE LLC, Broomfield, CO (US)

( * ) Notice: Subject to any disclaimer, the term of this patent is extended or adjusted under 35 U.S.C. 154(b) by 236 days.

(21) Appl. No.: 13/171,400

(22) Filed: Jun. 28, 2011

(65) Prior Publication Data

US 2012/0078343 A1    Mar. 29, 2012

Related U.S. Application Data

(60) Provisional application No. 61/359,242, filed on Jun. 28, 2010.

(51) Int. Cl.
| | |
|---|---|
| A61F 2/958 | (2013.01) |
| A61F 2/962 | (2013.01) |
| A61M 25/00 | (2006.01) |
| A61M 25/01 | (2006.01) |
| A61M 25/10 | (2013.01) |

(52) U.S. Cl.
CPC ............. *A61F 2/958* (2013.01); *A61F 2/962* (2013.01); *A61M 25/0074* (2013.01); *A61M 2025/0058* (2013.01); *A61M 2025/0175* (2013.01); *A61M 2025/1081* (2013.01)

(58) Field of Classification Search
CPC ......... A61F 2/958; A61F 2/962; A61F 2/966; A61F 2/2433; A61F 2/2436
USPC ............... 623/1.11, 1.12, 2.11; 604/101.01, 604/101.05
See application file for complete search history.

(56) References Cited

U.S. PATENT DOCUMENTS

| | | |
|---|---|---|
| 3,014,024 A | 12/1961 | Lieberman et al. |
| 3,029,819 A | 4/1962 | Edward |
| 3,105,492 A | 10/1963 | Jeckel |
| 3,320,972 A | 5/1967 | High et al. |
| 3,409,914 A | 11/1968 | Jones |
| 3,548,417 A | 12/1970 | Kischer et al. |
| 3,562,820 A | 2/1971 | Braun |
| 3,588,920 A | 6/1971 | Wesolowski |
| 3,671,979 A | 6/1972 | Moulopoulos |

(Continued)

FOREIGN PATENT DOCUMENTS

| | | |
|---|---|---|
| EP | 1603493 | 12/2005 |
| EP | 2000115 | 5/2011 |

(Continued)

OTHER PUBLICATIONS

Affidavit of Dr. Paolo Angelini, M.D., signed Aug. 25, 2009.

(Continued)

*Primary Examiner* — Thomas McEvoy
(74) *Attorney, Agent, or Firm* — Fox Rothschild LLP

(57) ABSTRACT

A dual-balloon delivery catheter system includes a carrier segment that is a lead/carrier balloon or mandrel at a distal portion of a catheter. The carrier segment is sequentially arrayed with a more proximally positioned delivery segment, wherein the delivery segment is a delivery balloon or mandrel. The first carrier segment expands the stent-valve a sufficient amount to receive the delivery segment after the carrier segment is moved away from the sent-valve. The delivery segment is then positioned at the target site and the stent-valve is then deployed.

11 Claims, 10 Drawing Sheets

(56) References Cited

U.S. PATENT DOCUMENTS

| | | | |
|---|---|---|---|
| 3,709,175 | A | 1/1973 | Edwards et al. |
| 3,878,565 | A | 4/1975 | Sauvage |
| 3,945,052 | A | 3/1976 | Liebig |
| 3,966,401 | A | 6/1976 | Hancock et al. |
| 3,983,581 | A | 10/1976 | Angell et al. |
| 3,986,828 | A | 10/1976 | Hoffman, Jr. et al. |
| 4,011,947 | A | 3/1977 | Sawyer |
| 4,035,849 | A | 7/1977 | Angell et al. |
| 4,055,861 | A | 11/1977 | Carpentier et al. |
| 4,056,854 | A | 11/1977 | Boretos et al. |
| 4,060,081 | A | 11/1977 | Yannas et al. |
| 4,082,507 | A | 4/1978 | Sawyer |
| 4,084,268 | A | 4/1978 | Ionescu et al. |
| 4,106,129 | A | 8/1978 | Carpentier et al. |
| 4,164,045 | A | 8/1979 | Bokros et al. |
| 4,172,295 | A | 10/1979 | Batten |
| 4,218,782 | A | 8/1980 | Rygg |
| 4,222,126 | A | 9/1980 | Boretos et al. |
| 4,233,493 | A | 11/1980 | Nath et al. |
| 4,265,694 | A | 5/1981 | Boretos et al. |
| 4,291,420 | A | 9/1981 | Reul |
| 4,340,977 | A | 7/1982 | Brownlee et al. |
| 4,350,492 | A | 9/1982 | Wright et al. |
| 4,364,127 | A | 12/1982 | Pierce et al. |
| 4,388,735 | A | 6/1983 | Ionescu et al. |
| 4,423,525 | A | 1/1984 | Vallana et al. |
| 4,441,216 | A | 4/1984 | Ionescu et al. |
| 4,456,589 | A | 6/1984 | Holman et al. |
| 4,473,423 | A | 9/1984 | Kolff |
| 4,477,930 | A | 10/1984 | Totten et al. |
| 4,490,859 | A | 1/1985 | Black et al. |
| 4,517,687 | A | 5/1985 | Liebig et al. |
| 4,545,082 | A | 10/1985 | Hood |
| 4,597,762 | A | 7/1986 | Walter et al. |
| 4,600,533 | A | 7/1986 | Chu |
| 4,631,052 | A | 12/1986 | Kensey |
| 4,657,133 | A | 4/1987 | Komatsu et al. |
| 4,666,442 | A | 5/1987 | Arru et al. |
| 4,728,328 | A | 3/1988 | Hughes et al. |
| 4,743,231 | A | 5/1988 | Kay et al. |
| 4,759,758 | A | 7/1988 | Gabbay |
| 4,759,759 | A | 7/1988 | Walker et al. |
| 4,798,611 | A | 1/1989 | Freeman, Jr. |
| 4,801,299 | A | 1/1989 | Brendel et al. |
| 4,870,966 | A | 10/1989 | Dellon et al. |
| 4,883,458 | A | 11/1989 | Shiber |
| 4,892,539 | A | 1/1990 | Koch |
| 4,966,604 | A | 10/1990 | Reiss |
| 4,976,733 | A | 12/1990 | Girardot |
| 4,979,939 | A | 12/1990 | Shiber |
| 5,006,104 | A | 4/1991 | Smith et al. |
| 5,007,896 | A | 4/1991 | Shiber |
| 5,011,488 | A | 4/1991 | Ginsburg |
| 5,026,366 | A | 6/1991 | Leckrone |
| 5,032,128 | A | 7/1991 | Alonso |
| 5,047,041 | A | 9/1991 | Samuels |
| 5,047,050 | A | 9/1991 | Arpesani |
| 5,052,771 | A | 10/1991 | Williams et al. |
| 5,061,277 | A | 10/1991 | Carpentier et al. |
| 5,080,660 | A | 1/1992 | Buelna |
| 5,139,515 | A | 8/1992 | Robicsek |
| 5,163,955 | A | 11/1992 | Love et al. |
| 5,171,273 | A | 12/1992 | Silver et al. |
| 5,226,889 | A | 7/1993 | Sheiban |
| 5,261,878 | A | 11/1993 | Galindo |
| 5,282,847 | A | 2/1994 | Trescony et al. |
| 5,326,370 | A | 7/1994 | Love et al. |
| 5,326,371 | A | 7/1994 | Love et al. |
| 5,332,402 | A | 7/1994 | Teitelbaum |
| 5,336,616 | A | 8/1994 | Livesey et al. |
| 5,360,443 | A | 11/1994 | Barone et al. |
| 5,374,539 | A | 12/1994 | Nimni et al. |
| 5,376,110 | A | 12/1994 | Tu et al. |
| 5,383,927 | A | 1/1995 | De Goicoechea et al. |
| 5,411,552 | A | 5/1995 | Andersen et al. |
| 5,413,601 | A | 5/1995 | Keshelava |
| 5,415,633 | A | 5/1995 | Lazarus et al. |
| 5,449,384 | A | 9/1995 | Johnson |
| 5,476,506 | A | 12/1995 | Lunn |
| 5,480,424 | A | 1/1996 | Cox |
| 5,484,444 | A | 1/1996 | Braunschweiler et al. |
| 5,489,297 | A | 2/1996 | Duran |
| 5,500,015 | A | 3/1996 | Deac |
| 5,509,930 | A | 4/1996 | Love |
| 5,522,879 | A | 6/1996 | Scopelianos |
| 5,522,881 | A | 6/1996 | Lentz |
| 5,545,215 | A | 8/1996 | Duran |
| 5,549,664 | A | 8/1996 | Hirata et al. |
| 5,549,666 | A | 8/1996 | Hata et al. |
| 5,571,170 | A | 11/1996 | Palmaz et al. |
| 5,571,173 | A | 11/1996 | Parodi |
| 5,571,174 | A | 11/1996 | Love et al. |
| 5,578,071 | A | 11/1996 | Parodi |
| 5,578,072 | A | 11/1996 | Barone et al. |
| 5,582,168 | A | 12/1996 | Samuels et al. |
| 5,591,229 | A | 1/1997 | Parodi |
| 5,634,928 | A | 6/1997 | Fischell et al. |
| 5,645,559 | A | 7/1997 | Hachtman et al. |
| 5,653,749 | A | 8/1997 | Love et al. |
| 5,683,451 | A | 11/1997 | Lenker et al. |
| 5,713,953 | A | 2/1998 | Vallana et al. |
| 5,728,152 | A | 3/1998 | Mirsch, II et al. |
| 5,733,299 | A | 3/1998 | Sheiban et al. |
| 5,741,333 | A | 4/1998 | Frid |
| 5,746,775 | A | 5/1998 | Levy et al. |
| 5,769,780 | A | 6/1998 | Hata et al. |
| 5,782,914 | A | 7/1998 | Schankereli |
| 5,787,887 | A | 8/1998 | Klingenbeck-Regn |
| 5,840,081 | A | 11/1998 | Anderson et al. |
| 5,855,601 | A | 1/1999 | Bessler et al. |
| 5,861,028 | A | 1/1999 | Angell |
| 5,862,806 | A | 1/1999 | Cheung |
| 5,876,448 | A | 3/1999 | Thompson et al. |
| 5,895,420 | A | 4/1999 | Mirsch, II et al. |
| 5,957,949 | A | 9/1999 | Leonhardt et al. |
| 5,961,539 | A | 10/1999 | Northup et al. |
| 5,961,549 | A | 10/1999 | Nguyen et al. |
| 5,972,030 | A | 10/1999 | Garrison et al. |
| 5,976,179 | A | 11/1999 | Inoue |
| 6,004,328 | A | 12/1999 | Solar |
| 6,004,330 | A | 12/1999 | Midleman et al. |
| 6,010,531 | A | 1/2000 | Donlon et al. |
| 6,029,671 | A | 2/2000 | Stevens et al. |
| 6,045,576 | A | 4/2000 | Starr et al. |
| 6,053,938 | A | 4/2000 | Goldmann et al. |
| 6,091,984 | A | 7/2000 | Perelman et al. |
| 6,102,944 | A | 8/2000 | Huynh et al. |
| 6,117,169 | A | 9/2000 | Moe |
| 6,124,523 | A | 9/2000 | Banas et al. |
| 6,125,852 | A | 10/2000 | Stevens et al. |
| 6,126,686 | A | 10/2000 | Badylak et al. |
| 6,129,756 | A | 10/2000 | Kugler |
| 6,162,245 | A | 12/2000 | Jayaraman |
| 6,168,614 | B1 | 1/2001 | Andersen et al. |
| 6,168,619 | B1 | 1/2001 | Dihn et al. |
| 6,171,335 | B1 | 1/2001 | Wheatley et al. |
| 6,174,327 | B1 | 1/2001 | Mertens et al. |
| 6,186,999 | B1 | 2/2001 | Chen |
| 6,197,143 | B1 | 3/2001 | Bodnar |
| 6,214,055 | B1 | 4/2001 | Simionescu et al. |
| 6,221,091 | B1 | 4/2001 | Khosravi |
| 6,231,602 | B1 | 5/2001 | Carpentier et al. |
| 6,245,102 | B1 | 6/2001 | Jayaraman |
| 6,254,629 | B1 | 7/2001 | Inoue |
| 6,254,630 | B1 | 7/2001 | Inoue |
| 6,254,636 | B1 | 7/2001 | Peredo |
| 6,264,691 | B1 | 7/2001 | Gabbay |
| 6,269,819 | B1 | 8/2001 | Oz et al. |
| 6,270,526 | B1 | 8/2001 | Cox |
| 6,277,397 | B1 | 8/2001 | Shimizu |
| 6,277,555 | B1 | 8/2001 | Duran et al. |
| 6,287,335 | B1 | 9/2001 | Drasler |
| 6,293,970 | B1 | 9/2001 | Wolfinbarger |
| 6,312,462 | B1 | 11/2001 | McDermott et al. |

(56) References Cited

U.S. PATENT DOCUMENTS

| | | |
|---|---|---|
| 6,312,474 B1 | 11/2001 | Francis et al. |
| 6,334,873 B1 | 1/2002 | Lane et al. |
| 6,342,069 B1 | 1/2002 | Deac et al. |
| 6,350,278 B1 | 2/2002 | Lenker et al. |
| 6,350,282 B1 | 2/2002 | Eberhardt |
| 6,352,554 B2 | 3/2002 | De Paulis |
| 6,352,708 B1 | 3/2002 | Duran et al. |
| 6,358,275 B1 | 3/2002 | McIlroy et al. |
| 6,358,284 B1 | 3/2002 | Fearnot et al. |
| 6,371,980 B1 | 4/2002 | Rudakov et al. |
| 6,376,244 B1 | 4/2002 | Atala et al. |
| 6,378,221 B1 | 4/2002 | Ekholm, Jr. et al. |
| 6,383,171 B1 | 5/2002 | Gifford et al. |
| 6,391,333 B1 | 5/2002 | Li et al. |
| 6,409,755 B1 | 6/2002 | Vrba |
| 6,418,339 B1 | 7/2002 | Essenpries et al. |
| 6,425,916 B1 | 7/2002 | Garrison et al. |
| 6,432,712 B1 | 8/2002 | Wolfinbarger, Jr. et al. |
| 6,440,167 B2 | 8/2002 | Shimizu |
| 6,458,153 B1 | 10/2002 | Bailey et al. |
| 6,461,382 B1 | 10/2002 | Cao |
| 6,468,313 B1 | 10/2002 | Claeson et al. |
| 6,471,723 B1 | 10/2002 | Ashworth et al. |
| 6,482,227 B1 | 11/2002 | Solovay |
| 6,482,228 B1 | 11/2002 | Norred |
| 6,482,240 B1 | 11/2002 | Echmayer et al. |
| 6,491,719 B1 | 12/2002 | Fogarty et al. |
| 6,494,909 B2 | 12/2002 | Greenhalgh |
| 6,503,272 B2 | 1/2003 | Duerig et al. |
| 6,530,952 B2 | 3/2003 | Vesely |
| 6,534,004 B2 | 3/2003 | Chen et al. |
| 6,540,782 B1 | 4/2003 | Snyders |
| 6,553,681 B2 | 4/2003 | Ekholm, Jr. et al. |
| 6,558,418 B2 | 5/2003 | Carpentier et al. |
| 6,565,960 B2 | 5/2003 | Koob et al. |
| 6,569,200 B2 | 5/2003 | Wolfinbarger, Jr. et al. |
| 6,582,458 B1 | 6/2003 | White et al. |
| 6,582,462 B1 | 6/2003 | Andersen et al. |
| 6,582,464 B2 | 6/2003 | Gabbay |
| 6,599,524 B2 | 7/2003 | Li et al. |
| 6,610,088 B1 | 8/2003 | Gabbay |
| 6,624,890 B2 | 9/2003 | Backman et al. |
| 6,626,938 B1 | 9/2003 | Butaric et al. |
| 6,652,577 B2 | 11/2003 | Gianotti |
| 6,652,578 B2 | 11/2003 | Bailey et al. |
| 6,666,886 B1 | 12/2003 | Tranquillo et al. |
| 6,676,698 B2 | 1/2004 | McGuckin, Jr. |
| 6,682,537 B2 | 1/2004 | Ouriel et al. |
| 6,682,559 B2 | 1/2004 | Myers et al. |
| 6,685,739 B2 | 2/2004 | Dimatteo et al. |
| 6,696,074 B2 | 2/2004 | Dai et al. |
| 6,702,826 B2 | 3/2004 | Liddicoat et al. |
| 6,719,788 B2 | 4/2004 | Cox |
| 6,719,789 B2 | 4/2004 | Cox |
| 6,733,525 B2 | 5/2004 | Yang et al. |
| 6,736,823 B2 | 5/2004 | Darios et al. |
| 6,764,510 B2 | 7/2004 | Vidlund et al. |
| 6,773,456 B1 | 8/2004 | Gordon et al. |
| 6,773,457 B2 | 8/2004 | Ivancev |
| 6,790,229 B1 | 9/2004 | Berreklouw |
| 6,792,979 B2 | 9/2004 | Konya et al. |
| 6,802,319 B2 | 10/2004 | Stevens et al. |
| 6,802,806 B2 | 10/2004 | McCarthy et al. |
| 6,821,297 B2 | 11/2004 | Snyders et al. |
| 6,821,530 B2 | 11/2004 | Koob et al. |
| 6,830,584 B1 | 12/2004 | Seguin |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,608 B2 | 7/2005 | Liddicoat et al. |
| 6,916,338 B2 | 7/2005 | Speziali |
| 6,942,694 B2 | 9/2005 | Liddicoat et al. |
| 6,951,571 B1 | 10/2005 | Srivastava |
| 6,961,123 B1 | 11/2005 | Wang et al. |
| 6,977,231 B1 | 12/2005 | Matsuda |
| 6,986,735 B2 | 1/2006 | Abraham et al. |
| 7,004,925 B2 | 2/2006 | Navia et al. |
| 7,008,763 B2 | 3/2006 | Cheung |
| 7,011,688 B2 | 3/2006 | Gryska et al. |
| 7,018,404 B2 | 3/2006 | Holmberg et al. |
| 7,018,406 B2 | 3/2006 | Seguin et al. |
| 7,022,348 B2 | 4/2006 | Ketharananthan |
| 7,025,780 B2 | 4/2006 | Gabbay |
| 7,037,333 B2 | 5/2006 | Myers et al. |
| 7,039,446 B2 | 5/2006 | Ruchti et al. |
| 7,041,132 B2 | 5/2006 | Quijano et al. |
| 7,053,051 B2 | 5/2006 | Hendriks et al. |
| 7,060,092 B2 | 6/2006 | Kuribayashi et al. |
| 7,070,616 B2 | 7/2006 | Majercak et al. |
| 7,077,862 B2 | 7/2006 | Vidlund et al. |
| 7,084,082 B1 | 8/2006 | Shimizu |
| 7,138,226 B2 | 11/2006 | Vincek et al. |
| 7,153,324 B2 | 12/2006 | Case et al. |
| 7,160,322 B2 | 1/2007 | Gabbay |
| 7,164,145 B2 | 1/2007 | Shakespeare |
| 7,166,570 B2 | 1/2007 | Hunter et al. |
| 7,189,259 B2 | 3/2007 | Simionescu et al. |
| 7,213,601 B2 | 5/2007 | Stevens et al. |
| 7,214,242 B2 | 5/2007 | Abraham et al. |
| 7,232,461 B2 | 6/2007 | Ramer |
| 7,261,732 B2 | 8/2007 | Justino |
| 7,289,211 B1 | 10/2007 | Walsh, Jr. et al. |
| 7,309,461 B2 | 12/2007 | Kujawski et al. |
| 7,311,730 B2 | 12/2007 | Gabbay |
| 7,318,998 B2 | 1/2008 | Goldstein et al. |
| 7,329,279 B2 | 2/2008 | Haug et al. |
| 7,331,993 B2 | 2/2008 | White |
| 7,354,702 B2 | 4/2008 | Dai et al. |
| RE40,404 E | 6/2008 | Schmitt et al. |
| 7,381,218 B2 | 6/2008 | Schreck |
| 7,381,219 B2 | 6/2008 | Salahieh et al. |
| 7,399,315 B2 | 7/2008 | Iobbi |
| 7,427,291 B2 | 9/2008 | Liddicoat et al. |
| 7,431,725 B2 | 10/2008 | Stack et al. |
| 7,468,073 B2 | 12/2008 | Johnson et al. |
| 7,473,237 B2 | 1/2009 | Navia et al. |
| 7,481,838 B2 | 1/2009 | Carpentier et al. |
| 7,503,929 B2 | 3/2009 | Johnson et al. |
| 7,510,571 B2 | 3/2009 | Spiridigliozzi et al. |
| 7,510,575 B2 | 3/2009 | Spenser et al. |
| 7,524,330 B2 | 4/2009 | Berreklouw |
| 7,556,646 B2 | 7/2009 | Yang et al. |
| 7,566,343 B2 | 7/2009 | Jenson et al. |
| 7,585,321 B2 | 9/2009 | Cribier |
| 7,604,661 B2 | 10/2009 | Pavcnik et al. |
| 7,618,446 B2 | 11/2009 | Andersen et al. |
| 7,622,276 B2 | 11/2009 | Cunanan et al. |
| 7,628,805 B2 | 12/2009 | Spenser et al. |
| 7,648,676 B2 | 1/2010 | Mills et al. |
| 7,670,368 B2 | 3/2010 | Hill et al. |
| 7,708,775 B2 | 5/2010 | Rowe et al. |
| 7,758,632 B2 | 7/2010 | Hojeibane et al. |
| 7,780,722 B2 | 8/2010 | Thielen et al. |
| 7,789,909 B2 | 9/2010 | Andersen et al. |
| 7,846,203 B2 | 12/2010 | Cribier |
| 7,846,204 B2 | 12/2010 | Letac et al. |
| 7,871,431 B2 | 1/2011 | Gurm et al. |
| 7,892,281 B2 | 2/2011 | Seguin et al. |
| 7,914,576 B2 | 3/2011 | Navia et al. |
| RE42,395 E | 5/2011 | Wright et al. |
| 7,967,833 B2 | 6/2011 | Sterman et al. |
| 7,981,151 B2 | 7/2011 | Rowe |
| 8,002,825 B2 | 8/2011 | Letac et al. |
| 8,007,992 B2 | 8/2011 | Tian et al. |
| 8,057,540 B2 | 11/2011 | Letac et al. |
| 8,080,054 B2 | 12/2011 | Rowe |
| 8,105,375 B2 | 1/2012 | Navia et al. |
| 8,512,401 B2 | 8/2013 | Murray et al. |
| 8,512,403 B2 | 8/2013 | Navia et al. |
| 2001/0010017 A1 | 7/2001 | Letac et al. |
| 2001/0023372 A1 | 9/2001 | Chen et al. |
| 2001/0049558 A1 | 12/2001 | Liddicoat et al. |
| 2002/0005073 A1 | 1/2002 | Tompkins et al. |
| 2002/0028243 A1 | 3/2002 | Masters |

(56) References Cited

U.S. PATENT DOCUMENTS

| | | |
|---|---|---|
| 2002/0029783 A1 | 3/2002 | Stevens et al. |
| 2002/0032481 A1 | 3/2002 | Gabbay |
| 2002/0037940 A1 | 3/2002 | Koob et al. |
| 2002/0042621 A1 | 4/2002 | Liddicoat et al. |
| 2002/0091441 A1 | 7/2002 | Guzik |
| 2002/0095167 A1 | 7/2002 | Liddicoat et al. |
| 2002/0095994 A1 | 7/2002 | Vesely et al. |
| 2002/0123789 A1 | 9/2002 | Francis et al. |
| 2002/0128708 A1 | 9/2002 | Northup et al. |
| 2002/0151970 A1 | 10/2002 | Garrison et al. |
| 2003/0027332 A1 | 2/2003 | Lafrance et al. |
| 2003/0078659 A1 | 4/2003 | Yang |
| 2003/0102000 A1 | 6/2003 | Stevens et al. |
| 2003/0130727 A1 | 7/2003 | Drasler et al. |
| 2003/0130729 A1 | 7/2003 | Paniagua et al. |
| 2003/0130731 A1 | 7/2003 | Vidlund et al. |
| 2003/0149477 A1 | 8/2003 | Gabbay |
| 2003/0153974 A1 | 8/2003 | Spenser et al. |
| 2003/0187362 A1 | 10/2003 | Murphy et al. |
| 2003/0195620 A1 | 10/2003 | Huynh et al. |
| 2003/0204023 A1 | 10/2003 | Koob et al. |
| 2003/0212460 A1 | 11/2003 | Darois et al. |
| 2003/0212462 A1 | 11/2003 | Gryska et al. |
| 2003/0217415 A1 | 11/2003 | Crouch et al. |
| 2004/0024452 A1 | 2/2004 | Kruse et al. |
| 2004/0039442 A1 | 2/2004 | St. Goar |
| 2004/0055608 A1 | 3/2004 | Stevens et al. |
| 2004/0059418 A1 | 3/2004 | McKay et al. |
| 2004/0098092 A1 | 5/2004 | Butaric et al. |
| 2004/0158321 A1 | 8/2004 | Reuter et al. |
| 2004/0193261 A1 | 9/2004 | Berreklouw |
| 2004/0230285 A1* | 11/2004 | Gifford et al. ............... 623/1.11 |
| 2004/0243153 A1 | 12/2004 | Liddicoat et al. |
| 2004/0243229 A1 | 12/2004 | Vidlund et al. |
| 2005/0004668 A1 | 1/2005 | Aklog et al. |
| 2005/0027369 A1 | 2/2005 | Eldridge et al. |
| 2005/0043819 A1 | 2/2005 | Schmidt et al. |
| 2005/0096673 A1 | 5/2005 | Stack et al. |
| 2005/0113910 A1 | 5/2005 | Paniagua et al. |
| 2005/0137681 A1 | 6/2005 | Shoemaker et al. |
| 2005/0137682 A1 | 6/2005 | Justino |
| 2005/0142163 A1 | 6/2005 | Hunter et al. |
| 2005/0147562 A1 | 7/2005 | Hunter et al. |
| 2005/0147599 A1 | 7/2005 | Hunter et al. |
| 2005/0147643 A1 | 7/2005 | Hunter et al. |
| 2005/0148512 A1 | 7/2005 | Hunter et al. |
| 2005/0158274 A1 | 7/2005 | Hunter et al. |
| 2005/0159811 A1 | 7/2005 | Lane |
| 2005/0169958 A1 | 8/2005 | Hunter et al. |
| 2005/0169959 A1 | 8/2005 | Hunter et al. |
| 2005/0175657 A1 | 8/2005 | Hunter et al. |
| 2005/0187618 A1 | 8/2005 | Gabbay |
| 2005/0191248 A1 | 9/2005 | Hunter et al. |
| 2005/0228494 A1 | 10/2005 | Marquez |
| 2005/0241981 A1 | 11/2005 | Gupta et al. |
| 2005/0246035 A1 | 11/2005 | Wolfinbarger, Jr. et al. |
| 2005/0247320 A1 | 11/2005 | Stack et al. |
| 2005/0267529 A1 | 12/2005 | Crockett et al. |
| 2006/0004439 A1 | 1/2006 | Spenser et al. |
| 2006/0004443 A1 | 1/2006 | Liddicoat et al. |
| 2006/0020336 A1 | 1/2006 | Liddicoat |
| 2006/0025800 A1 | 2/2006 | Suresh |
| 2006/0041306 A1 | 2/2006 | Vidlund et al. |
| 2006/0074486 A1 | 4/2006 | Liddicoat et al. |
| 2006/0089708 A1 | 4/2006 | Osse et al. |
| 2006/0111733 A1 | 5/2006 | Shriver |
| 2006/0129225 A1 | 6/2006 | Kopia et al. |
| 2006/0134079 A1 | 6/2006 | Sih et al. |
| 2006/0140916 A1 | 6/2006 | Siani-Rose et al. |
| 2006/0173475 A1 | 8/2006 | Lafontaine et al. |
| 2006/0178740 A1 | 8/2006 | Stacchino et al. |
| 2006/0190074 A1 | 8/2006 | Hill et al. |
| 2006/0193885 A1 | 8/2006 | Neethling et al. |
| 2006/0195010 A1 | 8/2006 | Arnal et al. |
| 2006/0195183 A1 | 8/2006 | Navia et al. |
| 2006/0206203 A1 | 9/2006 | Yang et al. |
| 2006/0229701 A1 | 10/2006 | Gurm et al. |
| 2006/0240063 A9 | 10/2006 | Hunter et al. |
| 2006/0240064 A9 | 10/2006 | Hunter et al. |
| 2006/0259134 A1 | 11/2006 | Schwammenthal et al. |
| 2006/0259135 A1 | 11/2006 | Navia et al. |
| 2006/0259137 A1 | 11/2006 | Artof et al. |
| 2006/0265056 A1 | 11/2006 | Nguyen et al. |
| 2006/0287571 A1 | 12/2006 | Gozzi et al. |
| 2006/0292125 A1 | 12/2006 | Kellar et al. |
| 2007/0010857 A1 | 1/2007 | Sugimoto et al. |
| 2007/0043431 A1 | 2/2007 | Melsheimer |
| 2007/0050014 A1 | 3/2007 | Johnson |
| 2007/0050022 A1 | 3/2007 | Vidlund et al. |
| 2007/0056346 A1 | 3/2007 | Spenser et al. |
| 2007/0060932 A1 | 3/2007 | Stack et al. |
| 2007/0061008 A1 | 3/2007 | Salahieh et al. |
| 2007/0100426 A1 | 5/2007 | Rudakov et al. |
| 2007/0104395 A1 | 5/2007 | Kinigakis et al. |
| 2007/0128174 A1 | 6/2007 | Kleinsek et al. |
| 2007/0173861 A1 | 7/2007 | Strommer et al. |
| 2007/0203575 A1 | 8/2007 | Forster et al. |
| 2007/0213813 A1 | 9/2007 | Von Segessler et al. |
| 2007/0233228 A1 | 10/2007 | Eberhardt et al. |
| 2007/0250154 A1 | 10/2007 | Greenberg et al. |
| 2007/0263226 A1 | 11/2007 | Kurtz et al. |
| 2007/0276432 A1 | 11/2007 | Stack et al. |
| 2007/0276461 A1* | 11/2007 | Andreas et al. ............... 623/1.11 |
| 2008/0004686 A1 | 1/2008 | Hunt et al. |
| 2008/0009667 A1 | 1/2008 | Longhini et al. |
| 2008/0009940 A1 | 1/2008 | Cribier |
| 2008/0029105 A1 | 2/2008 | Stevens et al. |
| 2008/0039871 A1 | 2/2008 | Wallace et al. |
| 2008/0039926 A1 | 2/2008 | Majercak et al. |
| 2008/0058798 A1 | 3/2008 | Wallace et al. |
| 2008/0082113 A1 | 4/2008 | Bishop et al. |
| 2008/0102439 A1 | 5/2008 | Tian et al. |
| 2008/0133004 A1 | 6/2008 | White |
| 2008/0147182 A1 | 6/2008 | Righini et al. |
| 2008/0154356 A1 | 6/2008 | Obermiller et al. |
| 2008/0177381 A1 | 7/2008 | Navia et al. |
| 2008/0183280 A1 | 7/2008 | Agnew et al. |
| 2008/0183283 A1 | 7/2008 | Downing |
| 2008/0190989 A1 | 8/2008 | Crews et al. |
| 2008/0195200 A1 | 8/2008 | Vidlund et al. |
| 2008/0199843 A1 | 8/2008 | Haverich et al. |
| 2008/0200977 A1 | 8/2008 | Paul et al. |
| 2009/0005857 A1* | 1/2009 | Ischinger ............... 623/1.18 |
| 2009/0030511 A1 | 1/2009 | Paniagua et al. |
| 2009/0043383 A1 | 2/2009 | McGregor et al. |
| 2009/0054969 A1 | 2/2009 | Salahieh |
| 2009/0062907 A1 | 3/2009 | Quijano et al. |
| 2009/0112309 A1 | 4/2009 | Jaramillo et al. |
| 2009/0132032 A9 | 5/2009 | Cribier |
| 2009/0157175 A1 | 6/2009 | Benichou |
| 2009/0164005 A1 | 6/2009 | Dove et al. |
| 2009/0187241 A1 | 7/2009 | Melsheimer |
| 2009/0248149 A1 | 10/2009 | Gabbay |
| 2009/0254175 A1 | 10/2009 | Quijano et al. |
| 2009/0281609 A1 | 11/2009 | Benichou et al. |
| 2010/0030259 A1 | 2/2010 | Pavcnik et al. |
| 2010/0036479 A1 | 2/2010 | Hill et al. |
| 2010/0036484 A1 | 2/2010 | Hariton et al. |
| 2010/0043197 A1 | 2/2010 | Abbate et al. |
| 2010/0048987 A1 | 2/2010 | Khairkhahan |
| 2010/0049312 A1 | 2/2010 | Edoga et al. |
| 2010/0131054 A1 | 5/2010 | Tuval et al. |
| 2010/0161036 A1 | 6/2010 | Pintor et al. |
| 2010/0185277 A1 | 7/2010 | Braido et al. |
| 2010/0217382 A1 | 8/2010 | Chau et al. |
| 2010/0234878 A1 | 9/2010 | Hruska |
| 2010/0241069 A1* | 9/2010 | Hatten ............... 604/96.01 |
| 2010/0249918 A1 | 9/2010 | Zhang |
| 2010/0256749 A1 | 10/2010 | Tran et al. |
| 2010/0256751 A1 | 10/2010 | Rowe et al. |
| 2010/0312333 A1 | 12/2010 | Navia et al. |
| 2011/0004299 A1 | 1/2011 | Navia et al. |
| 2011/0015728 A1 | 1/2011 | Jimenez et al. |
| 2011/0040375 A1 | 2/2011 | Letac et al. |

(56) References Cited

U.S. PATENT DOCUMENTS

| | | |
|---|---|---|
| 2011/0087322 A1 | 4/2011 | Letac et al. |
| 2011/0137409 A1 | 6/2011 | Yang et al. |
| 2011/0146361 A1 | 6/2011 | Davidson et al. |
| 2011/0153009 A1 | 6/2011 | Navia et al. |
| 2011/0166636 A1 | 7/2011 | Rowe |
| 2011/0178597 A9 | 7/2011 | Navia et al. |
| 2011/0218619 A1 | 9/2011 | Benichou et al. |
| 2011/0224607 A1 | 9/2011 | Vogelbaum et al. |
| 2011/0240511 A1 | 10/2011 | Bolton et al. |
| 2011/0300625 A1 | 12/2011 | Paniagua et al. |
| 2011/0301700 A1 | 12/2011 | Fish et al. |
| 2012/0078343 A1 | 3/2012 | Fish |
| 2012/0078356 A1 | 3/2012 | Fish et al. |
| 2012/0095551 A1 | 4/2012 | Navia et al. |
| 2012/0158128 A1 | 6/2012 | Gautam et al. |
| 2012/0185038 A1 | 7/2012 | Fish et al. |
| 2012/0310041 A1 | 12/2012 | Paniagua et al. |
| 2013/0304201 A1 | 11/2013 | Navia et al. |
| 2014/0039613 A1 | 2/2014 | Navia et al. |

FOREIGN PATENT DOCUMENTS

| | | |
|---|---|---|
| EP | 1441672 | 9/2011 |
| EP | 2055266 | 2/2012 |
| EP | 1621162 | 5/2012 |
| EP | 2260796 | 2/2013 |
| JP | 09-501594 | 2/1997 |
| JP | 2001-500761 | 1/2001 |
| JP | 2005-103321 | 4/2005 |
| RU | 2355361 C | 5/2009 |
| WO | 91-17720 | 11/1991 |
| WO | 92-17118 | 10/1992 |
| WO | 98/29057 | 7/1998 |
| WO | 99/30646 | 6/1999 |
| WO | 00/12164 | 3/2000 |
| WO | 01-02031 | 1/2001 |
| WO | 03/047468 | 6/2003 |
| WO | 03-092554 | 11/2003 |
| WO | 2004/026124 | 4/2004 |
| WO | 2004/082527 | 9/2004 |
| WO | 2006-095342 | 9/2006 |
| WO | 2007-138572 | 12/2007 |
| WO | 2008/082527 | 7/2008 |
| WO | 2008/063537 | 8/2008 |
| WO | 2008/106531 | 9/2008 |
| WO | 2009-052188 | 4/2009 |
| WO | 2009-156471 | 12/2009 |
| WO | 2010/024801 | 3/2010 |
| WO | 2010/027363 | 3/2010 |
| WO | 2010/080594 | 7/2010 |
| WO | 2010/117541 | 10/2010 |
| WO | 2011-109433 | 3/2011 |
| WO | 2011-109450 | 9/2011 |
| WO | 2012-006124 | 1/2012 |
| WO | 2012/040643 | 3/2012 |
| WO | 2012/082952 | 6/2012 |

OTHER PUBLICATIONS

Affidavit of Dr. Gervasio A. Lamas, M.D., signed Sep. 3, 2009.
Andersen, H.R. et al., "Transluminal implantation of artificial heart valve" European Heart Journal, 1992, 13, pp. 704-708.
"Artificial heart valve" http://en.wikipedia.org/Artificial_heart_valve, printed May 13, 2009.
Bonhoeffer, Philipp M.D. et al., "Percutaneous Insertion of the Pulmonary Valve" J of the Amer College of Cardiology, vol. 39, No. 10, Elsevier Science, Inc. 2002, pp. 1664-1669, London, UK, and Paris, FR.
Bonhoeffer, Philipp et al., "Percutaeous replacement of pulmonary valve in a right-centricle to pulmonary-artery prosthetic conduit with valve dysfunction" Early Report, The Lacet, vol. 356, Oct. 21, 2000, p. 1403-1405.
Bonhoeffer, Philipp et al., "Transcatherter Implantation of a Bovine Valve in Pulmonary Position: A Lamb Study" Circulation J. of the Amer Heart Assoc, 2000; 102; 813-816.
Boudjemline, Younes et al., "Percutaneous pulmonary valve replacement in a large right ventricular outflow tract: An experimental study" J. Am. Coll. Cardiol. 2004; 43; 1082-1087.
Braga-Vilela, A. et al., "Extracellular Matrix of Porcine Pericardium; Biochemistry and Collagen Architecture" J. Membr Biol., 2008.
Breuer, Christopher K. M.D. et al., "Application of Tissue-Engineering Principles toward the Development of a Semilunar Heart Valve Substitute" Tissue Engineering, vol. 10, No. 11/12, 2004 pp. 1725-1736.
Cale, A.R. et al., "Revisited: a descending thorasic aortic valve to treat prosthetic valve insufficiency" Ann Thorac Surg, May 1993, 55(5), pp. 1218-2.
Cerrolaza, M et al., "A comparison of the hydrodynamical behaviour of three heart aortic prostheses by numerical methods".
"Collagen" http://en.wikipedia.org/wiki/Collagen, printed May 13, 2009.
Collins, J. J., Jr, "The Evolution of artificial heart valve" N. Engl J Med, Feb. 28, 1991; 324(9):624-6.
Corden, J. et al., "The influence of open leaflet geometry on the haemodynamic flow characteristics of polyrethane trileaflet artificial heart valve" PubMed medline query, p. 1 of 1.
Cribier, Alain et al., "Percutaneious Transcatheter Implantation of an Aoritc Valve Prosthesis for Calcific Aortic Stenosis: First Human Case Description" Circulation J of the Amer Heart Assoc, originally published online Nov. 25, 2002.
Edwards Lifesciences Receives FDA Approval for New Heart Valve, http:www.medicalnewstoday.com/articles/149588.php, dated May 11, 2009.
Fish, R. David, "Percutaneous Heart Valve Replacement: Enthusiasm Tempered" Circulation J of the Amer Heart Assoc, 2004; 110; 1876-1878.
Fishbein, M.C. et al., "Cardiac pathology after aortic valve replacement using Hufnagel trileaflet prostheses: study of 20 necropsy patients" Ann Heart J., Apr. 1975, 89(4), pp. 443-448.
Gloeckner, D. Claire et al., "Mechanical Evaluation and Design of a Multilayered Collagenous Repair Biomaterial" J. of Biomedical Materials Research Part A, vol. 52 Iss 2, pp. 365-373, Published online Aug. 15, 2000, Wiley Periodicals, Inc.
Grube E., et al., "Progress and Current Status of Percutaneous Aortic Valve Replacement: Results of Three Device Generations of the CoreValve Revalving System", Circ. Cardiovasc Intervent. 2008;1:167-175 (abstract).
Hanlon, JG et al., "Pre-use intraoperative testing of autologous tissue for valvular surgery: a proof of concept study" J. Heart Valve Dis, Nov. 1999; 8(6); pp. 614-623.
Bech-Hanssen, Odd, M.D. et al., "Aortic Prosthetic Valve Desing and Size: Relation to Doppler Echocardiographic Finding and Pressure Recovery—An In Vitro Study" J. Am Soc Echocardiography 2000; 13:39-50.
Hasenkam, J.M. et al., "A model for acute haemodynamic studies in the ascending aorta in pigs" Cardiovasc Res, Jul. 1988, 22(7), pp. 464-471.
Hiester,E.D. et al., "Optimal bovine pericardial tissue selection sites. I. Fiber architecture and tissue thickness measurements." J. Biomed Mater Res, Feb. 1, 1998; 39(2):207-14.
Hufnagel, Charles A., M.D., "Basic Concepts in the Development of Cardiovascular Prosthes" The American Journal of Surgery, vol. 137, Mar. 1979.
Hufnagel, Charles.A., MD et al., "In the beginning. Surgical Correction of Aortic Insufficiency" 1954; Ann Thorac Surg May 1989; 47(3), pp. 475-476.
Hufnagel, Charles.A., MD et al., "Late follow-up of ball-valve prostheses in the descending thoracic aortia", J. Throrac Cardiovasc Surg, Dec. 1976, 72(6), pp. 900-909.
Hufnagel, Charles.A., MD et al., "Surgical Correction of Aortic Insufficiency" Surgery vol. 35, May 1954 No. 5.
Hufnagel, Charles A., "Vessels and Valves", Sec. 1: Development of Cardiac Surgery, Chap 7, pp. 43-55.
"Introduction to Stereomicroscopy", http://www.microscopyu.com/articles/stereomicroscopy/stereointro.html, May 13, 2009.

(56) References Cited

OTHER PUBLICATIONS

IOPATCH(R) Tutoplast(R) Processed Pericardium Directions for Use; http://www.iopinc.com/surgeons_and_medical_professionals/iopatch/directions.asp, printed on Jun. 2, 2009.

Knudsen, LL et al., "Catheter-implanted prosthetic heart valves. Transluminal catheter implantation of a new expandable artificial heart valve in the descending thoracic aorta in isolated vessels and closed chest pigs" Int J. Artif Organs, May 1993, 16(5); pp. 253-262.

Lax, Jorge A., M.D., et al. "Estimation of the Ejection Fraction in Patients with Myocardial Infarction Obtained from the Combined Index of Systolic and Diastolic Left Ventricular Function: A New Method" J of the American Soc of Echocardiography, vol. 13, No. 2.

Liao, Jun et al., "Molecular orientation of collagen in intact planar connective tissues under biaxial stretch" Acta Biomateriala, vol. 1, Iss. 1, Jan. 2005, pp. 45-54.

Liao, K X et al., "Two-dimensional mechanical and ultrastructural correlates of bovine pericardium for prosthetic valves" ASAIO Trans, Jun. 1, 1991, 37(3); M341-51.

Ls, Yu et al., "New Polyurethane valves in new soft artificial heart" ASAIO Trans Jul.-Sep. 1989; 35(3), pp. 301-304.

Mirnajafi, A. et al. "The effects of collagen fiber orientation of the flexural properties of pericardial heterograft biomaterials" Biomaterials, Mar. 2005; 26(7): 795-804.

Mirzaie, M. et al., "A new storage solution for porcine aortic valves" Ann Thorac Cardiovasc Surg. Apr. 2007;13(2):102-9.

Moazami, N. et al., "Transluminal aortic valve placement. A feasibility study with a newly designed collapsible aortic valve" ASAIO J, Sep.-Oct. 1996, 42(5):M 381-5.

Nienaber C., M.D. et al., "Nonsurgical Reconstruction of Thoracic Aortic Dissection by Stent-Graft Placement" N. Eng. J. Med, May 20, 1999, col. 340, No. 20.

Noorlander, Maril L. et al., "A Quantitative Method to Determine the Orientation of Collagen Fibers in the Dermis" The J. of Histochemistry & Cytochemistry, vol. 50(11): 2002, pp. 1469-1474.

Nunn, D.B., "Structural Failure of Dacron Arterial Grafts" Seminars in Vascular Surgery, col. 12, No. 1 Mar. 1999, pp. 88-91.

Optical Microscope, Wikipedia, http://en.wikipedia.org/wiki/Stereomiscroscope, May 13, 2009.

Orthogonality, http://en.wikipedia.org/wiki/Orthogonal, May 13, 2009.

Paniagua, David, et al., Percutaneous Heart Valve in the Chronic In Vitro Testing Model, Circulation, 2002, pp. e51-e52, vol. 106, American Heart Association, US.

Paniagua, David et al, First Human Case of Retrograde Transcatheter Implantation of an Aortic Valve Prosthesis, Texas Heart Institute Journal, 2005, pp. 91-96, vol. 32, US.

"Pathak, CP et al., ""Treatment of bioprosthetic heart valve tissue with long chain alcohol solution to lowercalcification potential"" J Biomed Mater Res A. Apr. 1, 2004;69(1):140-4".

Pavenik, Susan, M.D., PhD et al., "Development and Initial Experimental Evaluation of a Prosthetic Aortic Valve for Transcatherter Placement" Cardivascular Radiology, Apr. 1992, pp. 151-154.

Pick, Adam, "True or False: An Edwards Lifescience Tissue Valve Replacement Requires 1,800 Hand-Sewn Stitches" http://heart-valve-surgery.com/heart-surgery-blog/2008/02/26. printed Aug. 13, 2010.

PCT International Search Report and Written Opinion, in Application PCT/US2011/042252, dated Apr. 6, 2011.

PCT International Search Report and Written Opinion, in Application PCT/US2011/053120, dated Apr. 27, 2012.

Chew, G.G. et al., Abstract for "Simulation of Damage in a Porcine Prosthetic Heart Valve" J. Med. Eng. Technol., Sep.-Oct. 1999; 23(5): 178-89.

Christie G.W. et al., Abstract for "On Stress Reduction in Bioprosthetic Heart Valve Leaflets by the Use of a Flexible Stent" J. Card Surg, Dec. 1991; 6(4) pp. 476-481.

PCT International Preliminary Report on Patentability, in Application PCT/US2011/042252, dated Dec. 28, 2012.

Non-Final Office Action issued in U.S. Appl. No. 13/038,260, dated Jun. 29, 2012.

PCT International Search Report and Written Opinion, in Application PCT/US2011/064989, dated Jun. 28, 2012.

Paniagua, David et al., Abstract 4622: "Percutaneous Implantation of a Low Profile, Dry Membrane, Heart Valve in an Integrated Delivery System in the Aortic and Pulmonary Positions: One-month Animal Results," Circulation, American Heart Association, Inc., 2009; 120: S982.

Notice of Allowance and Examiner Initiated Interview Summary issued in U.S. Appl. No. 13/038,361, dated Dec. 18, 2012.

Pohl, M. et al., "In vitro testing of artificial heart valves; comparison between Newtonian and non-Newtonian fluids" Artif Argns, Jan. 1996; 20(1); pp. 37-46.

Purinya, B. et al., "Biomechanical and Structural Properties of the Explanted Bioprosthetic Valve Leaflets" J. of Biomechanis, vol. 27, Iss 1, Jan. 1994 pp. 1-11 Elsevier Science Ltd, 1993.

Sacks, M S et al., "Collagen fiber architecture of bovine pericardium" ASAIO J, Jul. 1, 1994, 40(3):M632-7.

Sacks, M S et al., "A small angle light scattering device for planar connective tissue miscrostructural analysis" Ann Biomed Eng, Jul. 1, 1997, 254(4); 678-89.

Sacks, Michael S, "Incorporation of experimentally-derived fiber orientation into a structural constitutive model for planar collagenous tissues" J. Biomech Eng, Apr. 1, 2003, 125(2); 280-7.

Sacks, Michael S. et al., "Quantification of the fiber architecture and biaxial mechanical behavior of porcine intestinal submucosa" J of Biomedical Research, vol. 46, Iss 1, Jul. 1999, pp. 1-10.

Samouillan, V. et al., " Comparison of chemical treatments on the chain dynamics and thermal stability of bovine pericardium collagen" J Biomed Mater Res A. Feb. 1, 2003;64(2):330-8.

Schoen, Frederick J., "Tissue heart valves: Current challenges and future research perspectives" J of Biomedical Materials Research, vol. 47, Iss 4, Dec. 15, 1999, pp. 439-465.

Sellaro, Tiffany L., "Effects of Collagen Orientation on the Medium-Term Fatigue Response of Heart Valve Biomaterials" 2003, (published thesis) pp. 40-45.

Sellaro, Tiffany L. et al., "Effects of Collagen Fiber Orientation on the Response of Biologically Derived Soft Tissue Biomaterials to Cyclic Loading" J. Biomed Mater Res A Jan. 1, 2007; 80(1): 194-205); published online Oct. 13, 2006 by Wiley InterScience.

Shandas, Robin PhD et al., "A Method for Determining the Reference Effective Flow Areas for Mechanical Heart Valve Prostheses" Circulation Apr. 25, 2000.

Shen, Ming et al., "Effect of ethanol and ether in the prevention of calcification of bioprostheses" Ann Thorac Surg. May 2001;71(5 Suppl):S413-6.

Shen, Ming et al., "Protein adsorption in glutaraldehyde-preserved bovine pericardium and porcine valve tissues" The Annals of Thoracic Surgery, 2001; 71:409-409.

Simionescu, D et al., "Mapping of glutaraldehyde-treated bovine pericardium and tissue selection for bioprosthetic heart valve" J. Biomed Mater Res, Jun. 1, 1993:27(6):697-704.

Sun, Wei et al., "Response of heterograft heart valve biomaterials to moderate cyclic loading" J Biomed Mater Res A, Jun. 2004, 69(4); 658-69.

Topol, Eric J., "Textbook of Interventional Cardiology", 1990, Chs. 43-44, pp. 831-867.

Vyavahare, Narendra et al., "Mechanisms of bioprosthetic heart valve failure: Fatigue causes collagen denaturation and glycosaminoglysan loss" J of Biomedical Research, vol. 446, Iss 1, Jul. 1999, pp. 44-50.

Vyavahare, NR et al., "Prevention of Glutaraldehyde-Fixed Bioprosthetic Heart Valve Calcification by Alcohol Pretreatment: Further Mechanistic Studies" J Heart Valve Dis. Jul. 2000;9(4):561-6.

Werner, S. et al., "Testing the Hydrodynamic properties of heart valve prostheses with a new test apparatus", Biomed Tech (Berl) Sep. 1994; 30(9); pp. 204-210.

Wiegner, A W et al., "Mechanical and structural correlates of canine pericardium" Circ Res, Sep. 1, 1981m 49(3); 807-14.

Yasui, Takeshi et al., "Determination of collagen fiber orientation in human tissue by use of polarization measurement of molecular second-harmonic-generation light", Applied Optics, vol. 42, No. 14, May 10, 2004, pp. 2861-2867.

(56) References Cited

OTHER PUBLICATIONS

Zioupos, P. et al., "Anisotropic Elasticity and Strength of Glutaraldehyde Fixed Bovine Pericardium for Use in Pericardial Bioprosthetic Valves" J. Biomed Mater Res., Jan. 1994, 28(1):49-57.
Zioupos, P. et al., "Mechanical and Optical anisotrophy of bovine pericardium" Med Biol Eng Comput, Jan. 1992; 30(1); pp. 76-82.
Supplemental Declaration Under 37 CFR 1.131 by inventors filed in U.S. Appl. No. 10/887,688, filed Dec. 15, 2008.
Office Action issued in U.S. Appl. No. 10/887,688, dated Nov. 28, 2007.
Final Office Action issued in U.S. Appl. No. 10/887,688, dated Jul. 15, 2008.
Office Action issued in U.S. Appl. No. 10/887,688, dated Mar. 16, 2009.
Examiner Interview Summary issued in U.S. Appl. No. 10/887,688, dated Jun. 12, 2009.
Final Office Action issued in U.S. Appl. No. 10/887,688, dated Mar. 2, 2010.
Supplemental Declaration Under 37 CFR 1.131 by inventors filed in U.S. Appl. No. 10/887,688, filed Sep. 14, 2009.
Supplemental Declaration Under 37 CFR 1.131 by inventors filed in U.S. Appl. No. 10/887,688, filed Feb. 28, 2008.
Examiner Interview Summary issued in U.S. Appl. No. 10/887,688, dated Jul. 26, 2010.
Office Action issued in U.S. Appl. No. 10/887,688, dated Feb. 12, 2012.
Office Action issued Sep. 29, 2010, issued in U.S. Appl. No. 12/228,192.
Examiner Interview Summary, dated Apr. 5, 2011 in U.S. Appl. No. 12/228,192.
Final Office Action issued Jul. 14, 2011, in U.S. Appl. No. 12/228,192.
Office Action issued in U.S. Appl. No. 10/037,266, dated May 8, 2003.
Final Office Action issued in U.S. Appl. No. 10/037,266, dated Mar. 9, 2004.
PCT International Search Report and Written Opinion, in Application PCT/US2011/026763, dated Nov. 14, 2011.
PCT Written Opinion, in Application PCT/US2011/026741, dated Nov. 28, 2011.
Applicants' Reply to Written Opinion, filed Feb. 28, 2012, in App. PCT/US2011/026741.
U.S. Appl. No. 13/243,980, filed Sep. 23, 2011.
PCT Application No. PCT/US11/53120, filed on Sep. 23, 2011.
U.S. Appl. No. 13/326,196, filed Dec. 14, 2011.
PCT Application No. PCT/US11/64989, filed on Dec. 14, 2011.
U.S. Appl. No. 13/367,252, filed Jun. 28, 2011.
Office Action in Chinese Application No. 201180041521.6, dated Jul. 30, 2014.
Office Action in Australian Application No. 2011276503, dated Jun. 12, 2014.
Mendelson, Karen et al., "Heart Valve Tissue Engineering: Concepts, Approaches, Progress, and Challenges" Ann Biomed Eng, Dec. 2006; 34(12); pp. 1799-1819; published online Oct. 12, 2006 doi:10.1007/s/10439-006-9163-z.
Sacks, M S et al., "Bioprosthetic heart valve heterograft biomaterials: structure, mechanical behavior and computational simulation" Expert Rev Med Devices, Nov. 2006; 3(6): pp. 817-834 (Abstract only).
Schmidt, Dorthe et al., "Tissue engineering of heart valves using decellularized xenogeneic of polymeric starter matrices" Philos Trans R Soc Lond B Bio Sci., Aug. 29, 2007, 362(1484); 1505-1512; published online Jun. 22, 2007, doi: 10.1098/rstb.2007.2131.
Hilbert et al., "Biomechanics: Allograft Heart Valves," Cardiac Reconstructions with Allograft Tissues, Springer, New York (2005), pp. 210-212.
Office Action issued in Chinese Application No. 201180041521.6, dated Apr. 15, 2015.
Office Action issued in Japanese Application No. 2013-518589, dated May 7, 2015.

* cited by examiner

End View
(Sheath 524 Not Shown)

METHOD AND APPARATUS FOR THE ENDOLUMINAL DELIVERY OF INTRAVASCULAR DEVICES

CROSS-REFERENCE TO RELATED PATENT APPLICATION

The present application claims the benefit of U.S. Provisional Patent Application No. 61/359,242 filed on Jun. 28, 2010, the content of which is incorporated herein by reference in its entirety.

FIELD

Embodiments of the one or more present inventions relate to surgical methods and apparatus in general, and more particularly to surgical methods and apparatus for the endoluminal delivery of intravascular devices to a site within the body.

For the purposes of illustration but not limitation, embodiments of the one or more present inventions will hereinafter be discussed in the context of delivering a percutaneous heart valve to a valve seat located within the heart; however, it should be appreciated that at least one embodiment of the one or more present inventions is also applicable to other endoluminal delivery applications.

BACKGROUND

Percutaneous aortic valves, such as those available from Edwards Lifesciences LLC (Irvine, Calif.) under the tradename SAPIEN® typically utilize an expandable frame having valve leaflets attached thereto. This expandable frame essentially comprises a stent, with the valve leaflets (preferably in the form of tissue membrane) attached to a portion thereof. For this reason, these percutaneous aortic valves are commonly referred to as "stent-valves". Typically, the percutaneous aortic stent-valve is compressed down upon a deflated balloon catheter, the combined assembly is then inserted into the femoral artery through a covering sheath, and then the combined assembly is delivered endoluminally through the iliac artery and aorta to the valve seat. At the valve seat, the balloon is used to expand the stent so that the stent-valve is set at the valve seat, then the balloon is deflated, and finally the balloon catheter is withdrawn, whereupon the leaflets of the stent-valve act in place of the natural leaflets of the diseased aortic valve.

Percutaneous heart valves of the sort described above currently show great promise, particularly for elderly and/or otherwise infirm patients who cannot tolerate the trauma of conventional open heart valve replacement procedures.

Unfortunately, current percutaneous heart valve systems require the use of relatively large delivery/deployment apparatus. More particularly, since the internal balloon must be capable of expanding the stent portion of the stent-valve to the full size of the natural valve seat, and since the deflated size of a balloon having this full-expansion capability is relatively large, and since the stent-valve must be disposed circumferentially outboard of the balloon, the overall size of the delivery/deployment apparatus is necessarily large. By way of example but not limitation, the Edwards SAPIEN® delivery/deployment apparatus is typically approximately 7 to 8 mm in diameter.

Clinically, this can present a significant problem for the surgeon, since the preferred access to the vascular system of the patient is via the femoral artery, with subsequent delivery to the aortic valve seat via the iliac artery and aorta. However, the femoral artery is typically only about 5 to 8 mm in diameter, and this 5-8 mm range is for the general population as a whole—elderly female patients, who are expected to make up a substantial percentage of the candidate population for percutaneous aortic valve replacement, are on the smaller end of this range (e.g., perhaps 5-6 mm in diameter). Thus, it can be difficult or even impossible to pass the 7-8 mm (diameter) SAPIEN® device through the 5-6 mm (diameter) femoral artery of an elderly female patient, particularly where the femoral artery is tortuous, stenotic and/or occluded. Surgical incision has sometimes been required in order to gain access to a higher level of the ilio-femoral artery (e.g., within the pelvis) that is large enough to accommodate the stent-valve assembly. However, this approach is generally more invasive, and often leads to complications such as substantial bleeding and artery obstruction.

Referring now to FIG. 1, a schematic side view of a catheter-deliverable device, or stent-valve, known in the prior art is shown. Accordingly, FIG. 1 illustrates a schematic longitudinal cross-sectional view of catheter-deliverable device frame 10. The stent-valve may have an expanded diameter of approximately 25 mm. That is, the diameter D of external frame of deliverable device as fabricated and ready for mounting, is for example, 25 mm. However, the stent-valve can be compressed to approximately 4 mm in diameter. Accordingly, the dashed arrows of FIG. 1 show the device mechanically compressed 14 in mounting onto a catheter. The minimum achievable diameter Dmin of the fully compressed device (as limited by device mechanics and geometry) is, for example, 12 Fr (4 mm). FIG. 2 is a schematic longitudinal cross-sectional view of a typical large-diameter delivery balloon catheter (inflatable to diameter 25 mm) shown in a deflated state, e.g. 12 Fr (4 mm). As shown in FIG. 2, to achieve expansion of the stent-valve, it may be mounted on a typical prior art large-diameter delivery balloon catheter that is inflatable to a diameter of 25 mm. Accordingly, in FIG. 2 a shaft or balloon catheter 20 is shown (inflation lumen is omitted for clarity) having guide wire lumen 22. The balloon catheter further includes a compacted material of the deflated balloon 24. Compression of device 10 and reduction of its diameter is limited by size of the underlying catheter upon which it is mounted. The combined diameter, for example, 18 Fr (6 mm) of the device 10 mounted on balloon catheter 20 remains greater than minimum achievable diameter of device alone, for example 12 Fr (4 mm). However, the combined diameter of the stent-valve mounted on to the large-diameter delivery balloon catheter is perhaps 18 Fr or 6 mm, which is too large to insert into some patient's femoral artery.

For the foregoing reasons, there is a substantial need for a new and improved method and apparatus for the endoluminal delivery of intravascular devices to a site within the body.

SUMMARY

It is to be understood that embodiments of the one or more present inventions include a variety of different versions or embodiments, and this Summary is not meant to be limiting or all-inclusive. This Summary provides some general descriptions of some of the embodiments, but may also include some more specific descriptions of other embodiments.

When first considered, a solution associated with the difficulty of placing a stent-valve in a relatively small femoral artery appears to be use of a small delivery device. Accordingly, a small-diameter delivery balloon initially appears to address the problem. Referring to FIG. 3, a schematic longitudinal cross-sectional view of typical small-diameter delivery balloon catheter (inflatable to diameter 10 mm) is shown in a deflated state, for example, 7 Fr (2.3 mm). A smaller diameter balloon catheter 30 allows for a mounted device 34 to be compressed to its minimum achievable diameter, for example 12 Fr (4 mm). However, and with continued reference to FIG. 3, if the small diameter delivery balloon catheter 30 is used, then while the stent-valve 34 can be compressed to a relatively small diameter, the small-diameter delivery balloon is incapable of fully expanding the stent-valve to 25 mm; that is, a small diameter delivery balloon may only be capable of expanding the stent-valve to approximately 10 mm in diameter, for example.

At least one embodiment of the one or more present inventions addresses the aforementioned problems associated with the prior art by providing a novel method and apparatus for the endoluminal delivery of intravascular devices to a site within the body, at least one embodiment of the one or more present inventions takes advantage of the principle of dividing the volume of the stent-valve delivery apparatus into smaller diameter parts for separate insertion into the vascular system of a patient (e.g., into a relatively small diameter access vessel such as the femoral artery) and then re-assembling those parts within another portion of the vascular system of the patient (e.g., in a larger diameter vessel such as the aorta) which can accommodate the full size of the assembled components. By dividing the balloon expansion task into two serially-deployed balloons, activated in a staged fashion, the stent-valve can be delivered with a smaller profile, yet full stent-valve expansion at the valve seat can be ensured. Accordingly, novel devices and methods are proposed that involve transfer of a deliverable device, such as a stent-valve, after insertion into the body from its "carrier segment" to another "delivery segment" which may reside on the same or separate catheters, and deployment of the stent-valve from that "delivery segment" that is capable of expansion to suitable diameter for the stent-valve.

In at least one embodiment of the one or more present inventions, the stent-valve can be pre-mounted within a packaged pre-assembled delivery system for ready transport and clinical use.

In a first preferred form of the one or more present inventions, the first "carrier" balloon and second "delivery" balloon are mounted on separate inserter elements for independent delivery to the larger blood vessel, such as the aorta, where the second "delivery" balloon is united with the then-partially-expanded stent-valve—in this form, each balloon is independently advanced to the aorta via its own inserter element.

In a second preferred form of the one or more present inventions, the first and second balloons are serially disposed on a single inserter element, with the first "carrier" balloon being mounted to the inserter element distal to (or, optionally, more proximal to) the second "delivery" balloon—in this form, a single inserter element is used to sequentially position the first "carrier" balloon and second "delivery" balloon relative to the stent-valve.

In a third preferred form of the one or more present inventions, the first "carrier" balloon and second "delivery" balloon are mounted on separate inserter elements, but these inserter elements are arranged in a co-axial fashion so as to permit a telescoping action between the two inserter elements (and hence a telescoping action between the first "carrier" balloon and the second "delivery" balloon). In this form, the first "carrier" balloon shaft, being coaxially mounted upon a leading guide wire, can act as something of a firmer guidewire for the second "delivery" balloon.

In addition to the foregoing, after initial expansion of the stent-valve via the first "carrier" balloon, the first "carrier" balloon catheter can be removed and replaced by a shaped catheter element in order to provide guidance and assistance in traversing the central arteries and crossing the plane of (and, optionally, preparing) the native valve seat. This shaped catheter element can be disposed on an inserter element distal to the second "delivery" balloon or to the first carrier balloon, if desired.

If desired, the first "carrier" balloon can alternatively be another expandable device, e.g., the first "carrier" balloon (which constitutes the mounting segment for the stent-valve) can be an expandable mandrel. Alternatively, the stent-valve may be initially mounted on a non-expanding element, that is, simply a low-profile mandrel or other segment of the delivery catheter.

It should be appreciated that while at least one embodiment of the one or more present inventions has sometimes been discussed in the context of delivering a stent-valve to the aortic valve seat, it may also be used to deliver other valves to other valve seats, and/or for delivering other intravascular devices to other sites within the body.

It should also be appreciated that while at least one embodiment of the one or more present inventions is sometimes discussed in the context of advancing the stent-valve through the arterial system of the body, it may also be used to advance the stent-valve through the venous system of the body, or to endoluminally advance a device through some other luminal system of the body.

In at least one embodiment of the one or more present inventions, the covering sheath (through which the various components are advanced into the blood vessel) can be flexible and expandable so as to allow initial expansion of the stent-valve, and the exchange of the first "carrier" balloon and the second "delivery" balloon within the covering sheath, so that the apparatus is continuously protected.

It will be seen that at least one embodiment of the one or more present inventions provides a novel method and apparatus for the endoluminal delivery of an intravascular device to a site within the body.

Accordingly, at least one embodiment described herein is directed to a stent-valve and delivery system that is inserted separately into the femoral artery, then assembled inside the aorta, and thereafter advanced for deployment at the valve plane. This means that the limiting size of the artery (or vein, for the pulmonary valve) access diameter is determined by the largest single piece of the system—effectively the stent/valve itself. When the stent/valve is compressed without the balloon catheter, it is possible to deliver a valve into the circulation in as small as 14 French sheath rather than an 18 to 24 French, as has previously been achieved.

In at least one embodiment, an in-line dual-balloon delivery catheter system includes a carrier segment that is a lead/carrier balloon or mandrel at the distal portion of a catheter with the carrier segment arrayed in-line on a catheter shaft with a more proximally positioned delivery segment together at the distal portion of the catheter shaft. In essence, since the first "carrier" balloon only needs to expand the stent-valve a sufficient amount to receive the deflated second "delivery" balloon, the first "carrier" balloon can be quite small in its deflated condition. Moreover, the stent-valve, unrestricted by the traditional need for mounting on a single, relatively large deployment balloon, can be compressed to its minimum structural diameter for mounting on the relatively small first "carrier" balloon. As a result, the combined assembly (i.e., of carrier balloon catheter and stent-valve) can be much smaller in diameter than previous delivery devices at the time of accessing the vascular system of the patient. At the same time, by thereafter uniting the stent-valve with the second, larger "delivery" balloon, sufficient stent expansion can be provided to ensure secure valve seating.

In at least one embodiment, a woven wire "stent" with or without sheath investment is provided wherein its length is coupled to diameter. Nitinol or another alloy wire is formed in an expanded sheath shape and compressed by fraction on trailing wire ends. At the point of the procedure requiring distal sheath expansion, the traction is released to allow expansion to a mechanically biased open position. Alternatively, fraction wires may be attached to a distal end of the wire weave within the sheath and a traction force, there applied, causes simultaneous expansion and shortening of the distal end of the sheath, thereby advantageously releasing the underlying mounted stent-valve and exposing it for deployment.

In at least one embodiment a mechanism is provided for retaining a stent-valve frame on a delivery balloon by magnetic or electromagnetic means. The frame is preferably constituted of or contains ferrous metal elements. By such means, a stent-valve can be securely advanced through the vascular system without need for a covering sheath, thereby simplifying the delivery procedure and the system. The stent-valve is retained on the balloon segment by magnetic force.

In at least one embodiment, a device that utilizes magnetic force to deploy and, if desired, later retrieve a stent-valve is provided, the device using a magnetic force set at a level to permit ready balloon expansion of a stent-valve at a plane of the diseased native valve. As the frame of the stent-valve is pushed away from the magnet, retention force weakens, thereby allowing unimpeded final device expansion. A stronger magnet/electromagnet mounted on a separate catheter can be used to retrieve or reposition the stent-valve. In addition, a strong magnet mounted on a retrieval catheter can be used to retract the stent-valve frame from the native valve seat.

For the purposes of illustration but not limitation, embodiments of the one or more present inventions are hereinafter discussed in the context of delivering a prosthetic stent-valve to the aortic valve seat; however, it should be appreciated that at least one embodiment of the one or more present inventions is also applicable to other endoluminal delivery applications.

Accordingly, in at least one embodiment, a system for providing endoluminal delivery of a deliverable device through vasculature of a patient to a delivery site within the patient is provided, the system comprising:
  an outer delivery sheath including a distal section, wherein at least a portion of the outer delivery sheath is sized for insertion into the vasculature of the patient;
  a carrier segment located at a distal portion of a catheter shaft, the carrier segment having an outer surface sized to temporarily hold the deliverable device in the distal section of the outer delivery sheath, wherein at least a portion of the catheter shaft is located within and coaxial to the outer delivery sheath; and
  a delivery segment located coaxial to the outer delivery sheath, the delivery segment having an outer surface sized to radially fit within the deliverable device after detaching the deliverable device from the carrier segment when the deliverable device resides within the distal section of the outer delivery sheath, wherein the delivery segment is configured to deploy the deliverable device at the delivery site.

In addition to the foregoing, in at least one embodiment at least a portion of the distal section of the outer delivery sheath is expandable. In at least one embodiment, the at least a portion of the distal section of the outer delivery sheath comprises one or more electrically activated elements. In at least one embodiment, the at least a portion of the distal section of the outer delivery sheath comprises one or more piezo-ceramic elements. In at least one embodiment, the at least a portion of the distal section of the outer delivery sheath comprises a passively expandable material that is expandable upon application of an outward radial force applied by at least one of the carrier segment and the delivery segment. In at least one embodiment, the at least a portion of the distal section of the outer delivery sheath expands upon application of a tensile force to the at least a portion of the distal section.

In at least one embodiment, the distal section includes at least one of an internal projection and a narrowed area extending radially inward from an interior surface of the distal section.

In at least one embodiment, a portion of an internal surface of the outer delivery sheath further comprises a guide for retaining at least a portion of a longitudinally extending element configured to selectively manipulate at least a part of the outer delivery sheath or a structure coaxial to the outer delivery sheath. In at least one embodiment, a portion of an internal surface of the outer delivery sheath further comprises a guide, the guide comprising at least one of:
  (a) a lumen; and
  (b) a grommet;
wherein the guide retains at least one control line for selective retention of the deliverable device.

In at least one embodiment, the carrier segment and the delivery segment are both situated upon the catheter shaft. In at least one embodiment, the carrier segment is situated upon the catheter shaft, and wherein the delivery segment is associated with a delivery segment shaft that is coaxial to the catheter shaft and axially moveable relative to the catheter shaft. In at least one embodiment, the carrier segment is an expandable balloon having an expanded diameter smaller than an expanded diameter for the delivery segment. In at least one embodiment, the delivery segment is an expandable balloon having an expanded diameter larger than an expanded diameter for the carrier segment. In at least one embodiment, at least one of the carrier segment and the delivery segment is a mandrel. In at least one embodiment, the mandrel is expandable by mechanical or electromechanical means. In at least one embodiment, the mandrel is not expandable.

In at least one embodiment, the delivery segment is located axially proximal to the carrier segment. In at least one embodiment, the delivery segment is located axially distal to the carrier segment.

In at least one embodiment, one or both of the carrier segment and the delivery segment include at least one magnet or electromagnet to aid manipulation of the deliverable device.

In at least one embodiment an assembly for intravascular delivery of a deliverable device to a delivery site within a patient is provided, comprising:
  a first catheter including a first catheter shaft;
  a carrier segment situated along the first catheter shaft, the carrier segment configured to receive the deliverable device prior to inserting the first catheter within the patient; and
  a delivery segment sequentially positioned in an axial orientation relative to the carrier segment, wherein the delivery segment is configured to engage the deliverable device within the patient while the deliverable device is coaxial to at least a portion of the first catheter, and wherein the delivery segment is configured to thereafter deploy the deliverable device at the delivery site.

In at least one embodiment, the delivery segment is also situated along the first catheter. In at least one embodiment, the delivery segment is situated along a second catheter, the second catheter comprising a coaxial lumen through which passes the first catheter. In at least one embodiment, at least one of the first catheter and the second catheter comprise a curved distal portion.

One or more embodiments of the one or more present inventions also pertain to methods of delivering a device, such as a stent-valve, within a patient. Accordingly, in at least one embodiment, a method of delivering a deliverable device through vasculature of a patient to a target site within the patient is provided, comprising:

mounting the deliverable device on a selectively expandable carrier segment located along a catheter shaft, wherein at least a portion of the catheter shaft is located within and coaxial to an outer delivery sheath;

inserting the outer delivery sheath and catheter shaft into the patient;

moving the outer delivery sheath within the patient to position the selectively expandable carrier segment and the deliverable device near the target site;

partially expanding the deliverable device using the selectively expandable carrier segment while the deliverable device remains at least partially within the outer delivery sheath;

positioning a delivery segment radially within the deliverable device and partially expanding the delivery segment to facilitate engagement of the delivery segment with the deliverable device;

moving the delivery segment and deliverable device to the target site; and deploying the deliverable device at the target site by further expanding the delivery segment.

Various components are referred to herein as "operably associated." As used herein, "operably associated" refers to components that are linked together in operable fashion, and encompasses embodiments in which components are linked directly, as well as embodiments in which additional components are placed between the two linked components.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are understood by those of ordinary skill in the art to encompass obvious improvements and modifications thereto.

Additional advantages of at least one embodiment of the one or more present inventions will become readily apparent from the following discussion, particularly when taken together with the accompanying drawings.

BRIEF DESCRIPTION OF THE DRAWINGS

To further clarify the above and other advantages and features of the one or more present inventions, a more particular description of the one or more present inventions is rendered by reference to specific embodiments thereof which are illustrated in the appended drawings. It should be appreciated that these drawings depict only typical embodiments of the one or more present inventions and are therefore not to be considered limiting of its scope. The one or more present inventions are described and explained with additional specificity and detail through the use of the accompanying drawings in which.

Figure 1:
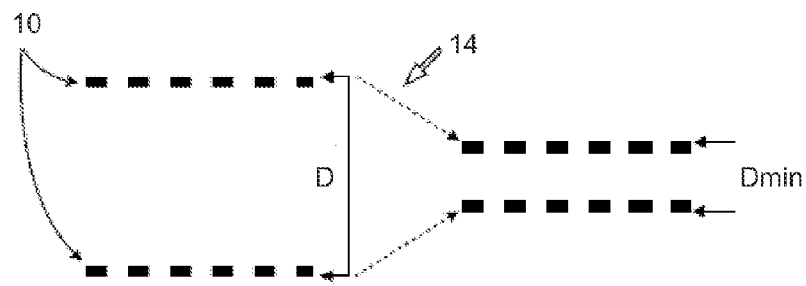
FIG. 1 is a schematic side view of a catheter-deliverable device frame (or stent-valve) known in the prior art.
Figure 2:
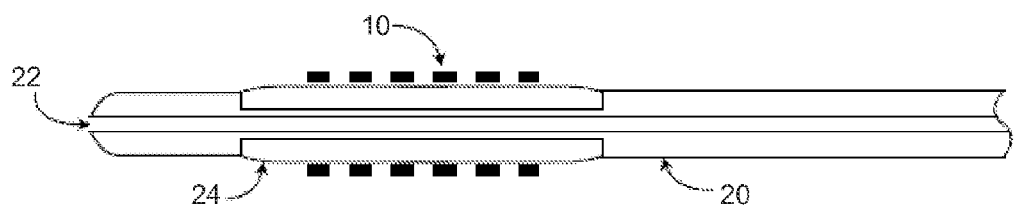
FIG. 2 is a schematic side view of a typical prior art large-diameter delivery balloon catheter in a deflated state.
Figure 3:
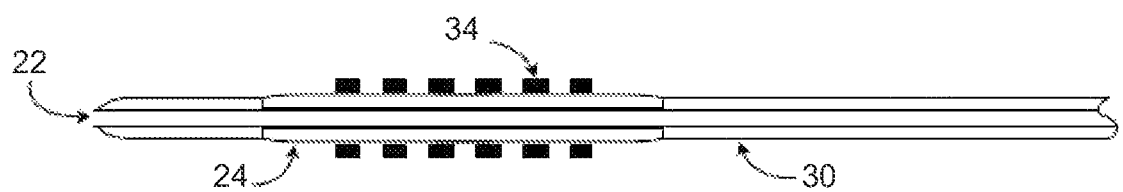
FIG. 3 is a schematic side view of a small-diameter delivery balloon catheter in a deflated state.

For the figures presented herein, balloons in a collapsed state are depicted as partially expanded to emphasize the difference in sizes. In addition, balloon catheter wire lumen and inflation lumens are omitted for clarity.

The drawings are not necessarily to scale.

DETAILED DESCRIPTION

Overview

In general, at least one embodiment of the one or more present inventions uses a serial approach for delivering and deploying the percutaneous aortic valve at the valve seat. This serial approach allows various components of the combined assembly (i.e., the various components of the balloon catheter and the stent-valve) to be separately introduced into the vascular system of the patient, each with its own minimized profile, so as to facilitate a low-profile endoluminal delivery of the system components into the large central blood vessels (e.g. the aorta) where, in a preferred sequence, these components are co-axially re-assembled prior to advancement to the target valve seat. As a result, at least one embodiment of the one or more present inventions facilitates femoral artery access to the aortic valve seat, even with patients having small femoral artery diameters (e.g., elderly female patients). In other words, since the various components of the system are not fully assembled at the time of insertion into the vascular system of the patient, and are only fully assembled at some point subsequent to insertion (e.g., within a larger diameter blood vessel upstream (farther inward) of the insertion site), a relatively large access vessel is no longer necessary—thereby making percutaneous heart valve therapy available for a larger patient population and with a lower risk of access site and blood vessel complications. By way of example but not limitation, where the intravascular device comprises an aortic stent-valve, the various components of the system can be easily introduced into a relatively narrow femoral artery and thereafter assembled in a larger upstream (farther inward) vessel (e.g., in the relatively wide aorta) before being advanced to and seated at the native aortic valve seat.

More particularly, at least one embodiment of the one or more present inventions preferably utilizes two separate balloons for a staged deployment of the stent-valve: a first, smaller-diameter "carrier" balloon for initial stent expansion (e.g., for preliminarily expanding the stent while the stent-valve is disposed in the descending aorta), and a second, larger-diameter "delivery" balloon for ultimate stent seating at the native valve seat. In one preferred form of at least one embodiment of the one or more present inventions, the stent-valve is mounted on the deflated first, smaller-diameter "carrier" balloon, then this relatively small assembly is introduced (within a covering sheath) into the relatively small femoral artery, advanced through the femoral artery, up through the iliac artery, and then into the relatively large descending aorta. The first, smaller-diameter "carrier" balloon is then inflated so as to expand the stent-valve to an intermediate diameter configuration that is large enough in diameter to receive the deflated second, larger-diameter "delivery" balloon. The first "carrier" balloon is then deflated, the first "carrier" balloon is withdrawn and replaced by the deflated second "delivery" balloon which, by partial inflation or other means, captures the stent-valve, and the assembly is then advanced up the descending aorta, ascending aorta, etc. to the native valve seat. The second "delivery" balloon is then inflated so as to set the stent-valve at the valve seat. Finally, the second "delivery" balloon is deflated and withdrawn from the surgical site.

In-Line Dual-Balloon Catheter Delivery System

With reference now to FIGS. 4A-4F, a stent-valve 120 may be advanced upon a first, smaller-diameter "carrier" balloon to the aorta and initially deployed (using the first, smaller-diameter "carrier" balloon) to an intermediate size, followed by co-axial exchange for the second, larger-diameter "delivery" balloon for advancement to the valve seat, and then further expansion of the stent-valve 120 at the valve seat. Alternatively, the stent-valve 120 may be advanced upon the carrier balloon all the way to the target valve seat and initially deployed before coaxial exchange for the delivery balloon and subsequent final expansion.

Figure 4A:
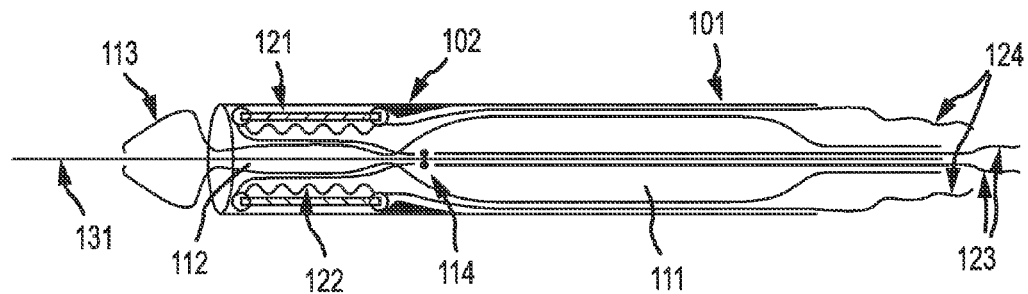
FIG. 4A is a side view of an in-line dual balloon delivery system in accordance with at least one embodiment of the one or more present inventions.

Referring now to FIG. 4A, an integrated system is shown in the form of an in-line dual-balloon delivery catheter system 100 that features an in-line dual-balloon catheter configuration. The configuration shown in FIG. 4A illustrates the in-line dual-balloon delivery catheter system 100 as it is being translated through the patient's body toward the target valve seat, such as the aortic valve. For the in-line dual-balloon delivery catheter system 100 described herein, the carrier segment 112 is a lead/carrier balloon or mandrel at the distal portion of a catheter with the carrier segment 112 arrayed in-line on a catheter shaft with a more proximally positioned delivery segment 111 together at the distal portion of the catheter shaft. Alternatively, the delivery segment may be positioned distal to the carrier segment. The carrier segment 112 and delivery segment 111 are, for the case of the balloon-expandable stent-valve 120 example in this discussion, expandable balloons, for example, but may also be mandrels or expandable mandrels.

Here, it is noted that, in at least one embodiment (including both the in-line dual-balloon delivery catheter system 100 and the telescoping delivery system 200), a delivery segment comprising a delivery mandrel can be non-expanding. By way of example and not limitation, the means by which the delivery segment retains the stent-valve may vary. For example, in addition to friction, the delivery segment may retain the stent-valve by use of magnetic force. For such an assembly, if the stent-valve (or other deliverable device) is self-expanding or actuated to expansion and retained on the delivery segment for release by some other means (electronic, heat, e.g.), then the delivery mandrel can be non-expanding.

For the configuration shown in FIG. 4A, an outer delivery sheath 101 having, for example, a lengthwise body 104 that is 14 French inside diameter, is coaxially situated over a guidewire 131, for example, a 0.035 inch diameter wire, whereupon the integrated pair of expandable balloons reside. It is noted that all sizes and material types presented herein are exemplary and are not intended to be limiting, nor should they be interpreted as limiting, unless otherwise claimed. Although not required, an optional nose cone 113 may be positioned distally of the carrier segment 112 to assist with insertion of the catheter into the artery and subsequent traverse through it. In the embodiment wherein the delivery segment is disposed distal to the carrier segment, said nose cone is positioned immediately distal to the delivery segment and approximated to the tip of the sheath. The carrier segment 112 is used to hold the stent-valve 120 in place within the outer delivery sheath 101 and provide initial expansion of the stent-valve 120. Thereafter, the delivery segment 111 is used to provide final expansion of the stent-valve 120 for deployment of the stent-valve 120 at the valve seat.

The in-line dual-balloon delivery catheter system 100 is assembled external to the body by passing the delivery catheter with its linearly arrayed carrier segment 112 and delivery segment 111 within the central coaxial lumen of the delivery sheath 101 such that the carrier segment 112 of the catheter extends and is fully exposed beyond the distal terminal opening of the delivery sheath 101. The catheter-deliverable device, such as the stent-valve 120 in this example, is then coaxially mounted upon the carrier segment 112 by collapsing and compressing it onto the carrier segment 112 such that friction between the two retains the device 120 upon the carrier segment 112. The carrier segment 112 with the catheter-deliverable device (stent-valve 120) mounted upon it is then retracted back (proximally) into the distal portion of the delivery sheath 101 so that the device is completely covered within the sheath 101. In some cases the tip of the carrier segment 112 may be extended beyond the end of the sheath. In such a case, partial expansion of the leading tip 113 of the carrier segment 112 (balloon or expandable mandrel) may be used to form the tapered "nose cone" as noted above, to facilitate advancement or insertion of the delivery system into the blood vessel. Alternatively, the carrier segment may be fabricated with a soft plastic tapered tip for this purpose.

In the example of retrograde (in relation to blood flow) passage of the delivery system carrying the catheter-deliverable device, initial guidance for passage of the delivery system is established by advancement of the guidewire 131 across the heart valve seat 141 into the upstream anatomic chamber, such as the left ventricle, there acting as a guiding rail for the coaxial advancement of the delivery system catheters. Then, at a point external to the body, by inserting the guide wire 131 into the distal tip of the carrier segment 112 of the delivery catheter, the assembled in-line dual-balloon delivery catheter system 100 with sheath 101 is then advanced into the body coaxially over the guidewire 131 to a position proximate to but short of the target anatomic site—in this case, the diseased heart valve seat 141.

Figure 4B:
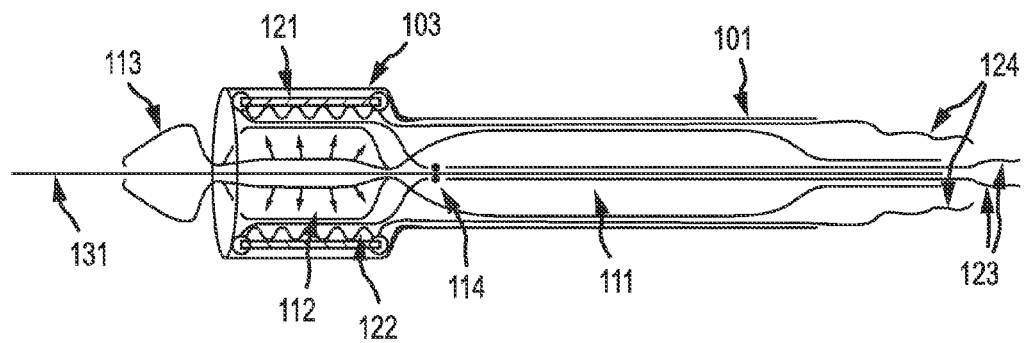
FIG. 4B is a side view of the system shown in FIG. 4A, wherein the carrier balloon is dilated to partially expand a stent-valve to accommodate the larger delivery balloon (catheter inflation ports, lumens, wire lumens not shown for clarity)

Referring now to FIG. 4B, when in the aorta, the leading carrier segment 112 is expanded as by balloon inflation, thus partially expanding the catheter-deliverable device (stent-valve 120) within the expandable distal segment 103 of the delivery sheath 101. That is, the carrier segment 112 is used to pre-dilate the stent-valve 120 so that the diameter of the stent-valve 120 is sufficient to accept the delivery segment 111 when the delivery segment 111 is at least partially deflated or not fully expanded. The outer delivery sheath may include an expandable and flexible distal segment to accommodate the partially expanded stent-valve 120 and hold the partially expanded stent-valve 120 in place. The carrier segment 112 is then contracted as by balloon deflation and advanced by advancing the delivery catheter out of the catheter-deliverable device (stent-valve 120) that is retained within the expanded distal segment 103 of the sheath 101. Optional shallow flanges 102 on the internal surface of the sheath 101 immediately proximal and/or distal to the mounted position of the device 120 can be used to assist in retention of the device during movement relating to the exchange of the carrier segment 112 for the delivery segment 111 with the advance of the delivery catheter. Alternatively, retention or control lines 123, 124 of wire or suture material may be attached to the device 120, as on the frame 121 of the stent-valve 120. Other forms of retaining force may be advantageously applied, such as by incorporating magnetic or electromagnetic elements within the delivery catheter shaft or within the sheath wall.

Figure 4C:
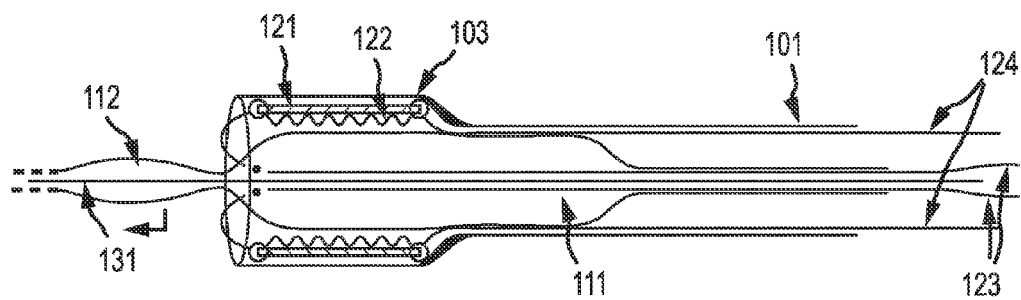
FIG. 4C is a side view of the system shown in FIG. 4B, wherein the deflated carrier balloon is advanced out of the partially expanded valve device as the delivery balloon is advanced into the stent-valve to "capture" or "dock" with the stent-valve.

Referring now to FIG. 4C, as the delivery catheter 110 is thus advanced, the delivery segment 111 integrated thereupon thus is also advanced within the sheath 101 to a position astride the catheter-deliverable device (stent-valve 120) within the delivery sheath 101, with the tip of the delivery catheter extended beyond the tip of the delivery sheath 101. More particularly, the delivery segment 111 is advanced axially to a position radially interior to the stent-valve 120. The delivery segment 111 is then partially expanded to contact the stent-valve 120.

Figure 4D:
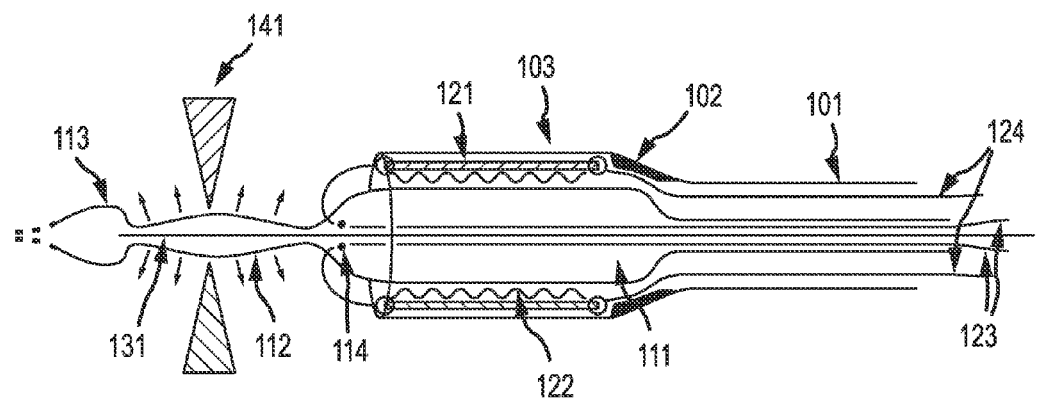
FIG. 4D is a side view of the system shown in FIG. 4C, wherein the carrier balloon is optionally inflated to facilitate crossing the plane of the diseased heart valve with the delivery system, and wherein the delivery balloon is positioned astride the stent-valve to capture and subsequently deploy the stent-valve.

Referring to FIG. 4D, with the delivery segment 111 positioned within the stent-valve 120, in at least one embodiment the carrier segment 112 is positioned at the valve seat and may be further expanded to facilitate advancement of the stent-valve 120 within the plane of the aortic valve. That is, if deemed desirable by the surgeon, the carrier segment 112 is temporarily expanded and then contracted or deflated within the plane of the valve seat to facilitate subsequent axial advancement of the delivery segment 111 that carries the stent-valve 120.

Figure 4E:
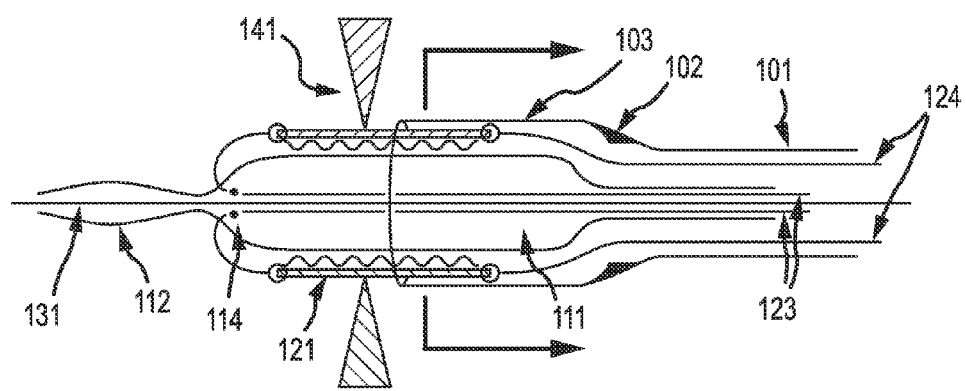
FIG. 4E is a side view of the system shown in FIG. 4D, wherein after the stent-valve is positioned in the plane of the heart valve, the sheath is withdrawn to expose the stent-valve in place at the heart valve seat and to allow for deployment if the stent-valve by expansion.
Figure 4F:
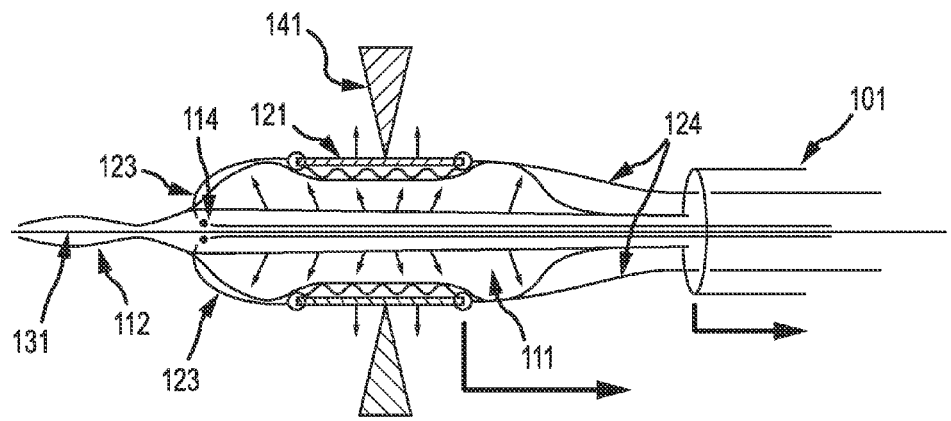
FIG. 4F is a side view of the system shown in FIG. 4E, wherein with the stent-valve is positioned at the valve seat and the sheath withdrawn, and wherein the delivery balloon then expanded to deploy the stent-valve.

With the projected tip of the delivery segment, and beyond that the carrier segment leading, the delivery catheter, catheter-deliverable device (stent-valve 120), and delivery sheath 101 are advanced together as a unit across the target anatomic plane (native heart valve seat 141, for example) to a position astride the target plane deemed suitable for deployment of the catheter-deliverable device (stent-valve 120). In the embodiment wherein the carrier segment is disposed proximal to the delivery segment this advancement occurs with the tip of the delivery segment leading the catheter assembly, and the carrier segment further proximal within the sheath. Referring now to FIG. 4E, after the delivery segment 111 is positioned in the plane of the target valve seat, the outer delivery sheath of the delivery system is withdrawn (as shown by the arrows in FIG. 4E) to expose the stent-valve 120; however, the stent-valve 120 remains undeployed because it continues to remain attached to the delivery segment 111. That is, the delivery sheath 101 is coaxially retracted with the delivery catheter held in place so as to expose the catheter-deliverable device (stent-valve 120) retained upon the delivery segment 111 at the site of deployment. The catheter-deliverable device (stent-valve 120) is then deployed by expansion of the delivery segment 111, such as by balloon inflation. Accordingly, and referring now to FIG. 4F, after the stent-valve 120 is exposed at the plane of the aortic valve, the delivery segment 111 is expanded to deploy the stent-valve 120. With full expansion and deployment of the catheter-deliverable device (stent-valve 120) the device is retained within the target anatomic plane (native heart valve seat 141). The delivery segment 111 is then contracted as by balloon deflation, function of the deployed device is confirmed, and the delivery catheter, delivery sheath 101, and guidewire 131 are retracted from the anatomic target area and removed from the body to complete the procedure.

In at least one embodiment, optional retention/control lines 123, 124 are released from valve frame 121 after successful deployment of stent-valve 120 is confirmed. Then balloon catheter 110 and guidewire 131 are removed from the valve seat 141 and withdrawn into sheath 101 for removal from the body.

In at least one embodiment, the carrier segment 112 is located axially proximal to the delivery segment 111. For such a configuration, the delivery segment 111 is advanced outside the sheath 101 and leads the assembly until the point the exchange is made. Then after the stent-valve 120 is partially expanded by the carrier segment 112, the delivery segment 111 is pulled back into the sheath 101 where the stent-valve 120 is retained, and the delivery segment 111 then captures the stent-valve 120. In this case, the tip of the delivery segment 111 at the tip of the sheath 101 will lead the further advance while the carrier segment 112 is sequestered more proximally in the sheath 101.

Telescoping Catheter Delivery System

Referring now to FIGS. 5A-5E, in an alternative embodiment, a telescoping delivery system 200 for a stent-valve 120 is provided wherein a delivery balloon catheter 210 is co-axially situated or "threaded" over a carrier balloon catheter shaft 224 associated with a carrier segment 221. Accordingly, the carrier segment 221 can be advanced axially independent of the axial position of the delivery balloon 211. As a result, the carrier segment shaft 224 acts as a guide rail for the delivery balloon catheter 210 and the stent-valve 120 that is then radially positioned exterior to the delivery balloon 211. Step-by-step illustrations are provided in the drawings and are described in the following paragraphs.

Figure 5A:
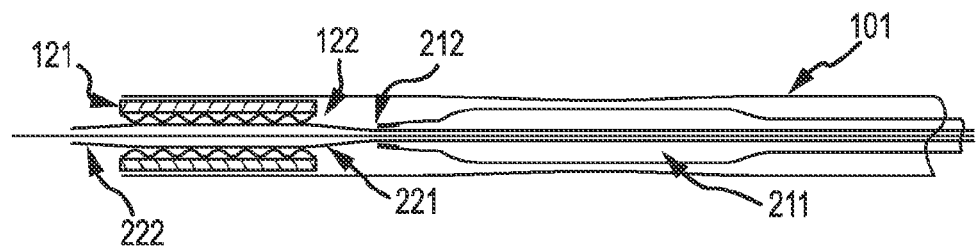
FIG. 5A is a side view of a catheter delivery system in accordance with another embodiment of the one or more present inventions, wherein a carrier balloon shaft passes through a central coaxial lumen of a delivery balloon (wherein the wall of central lumen is omitted for clarity)

Referring now to FIG. 5A, an outer delivery sheath 101 having, for example, a proximal shaft body with a 14 French inside diameter, is coaxially situated over a guidewire 131, whereupon a carrier segment shaft 224 and a delivery balloon shaft 214 are also co-axially situated. For the embodiment of the telescoping delivery system 200 described, the carrier segment 221 is a carrier balloon or mandrel at a distal portion of a carrier catheter 220 that is passed within the central lumen of a larger delivery catheter 210 that has a delivery segment 211 at its distal portion. By way of example and not limitation, the carrier segment shaft has a 0.035 inch outer diameter and is connected to the carrier segment 221 that is expandable to between 5-10 mm in diameter. The delivery segment 211 is, for the case of the balloon-expandable stent-valve 120 example, an expandable delivery balloon, for example. Accordingly, the delivery balloon may have an outside diameter of, for example, approximately 12-14 French when uninflated, and, in separate embodiments, is located axially either proximal or distal to the carrier segment 221.

The system is assembled external to the body by passing the carrier catheter 220 within the central coaxial lumen of the larger delivery catheter 210 such that the carrier segment 221 extends and is fully exposed beyond the tip 212 of the delivery catheter. These two catheters thus joined are then passed together through the delivery sheath 101 such that the carrier segment 221 of the carrier catheter 220 again extends and is fully exposed beyond the tip of the delivery sheath 101. The catheter-deliverable device, such as the stent-valve 120 in this example, is then coaxially mounted upon the carrier segment 221 by collapsing and compressing it onto the carrier segment 221 such that friction between the two retains the device 120 upon the carrier segment 221. The carrier segment 221 with the catheter-deliverable device (stent-valve 120) mounted upon it is then retracted back (proximally) into the delivery sheath 101 so that the device is completely covered within the sheath 101.

Figure 5B:
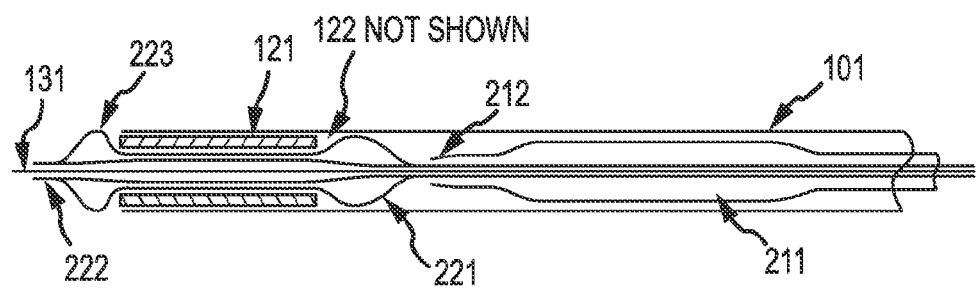
FIG. 5B is a side view of the system shown in FIG. 5A, wherein partial inflation of the leading carrier balloon may be used as a "nose cone" to facilitate insertion of the delivery catheter into a patient's artery.

Referring now to FIG. 5B, the lead carrier segment balloon 221 optionally may be partially expanded to hold the stent-valve 120 within the outer delivery sheath 101. In addition, in some cases the tip 222 of the carrier catheter and carrier segment 221 may be extended beyond the end of the sheath 101. In such a case, partial expansion of the leading tip 223 of the carrier segment 221 (balloon or expandable mandrel) may be used to form a tapered "nose cone" to facilitate advancement or insertion of the delivery system into the blood vessel. Alternatively, and as previously noted for the in-line dual-balloon delivery catheter system 100, the carrier catheter 220 for the telescoping delivery system 200 may be fabricated with a soft plastic tapered tip for this purpose.

In the example of retrograde (in relation to blood flow) passage of the delivery system carrying the catheter-deliverable device, initial guidance for passage of the delivery system is established by advancement of the guidewire 131 across the heart valve seat 141 into the upstream anatomic chamber, such as the left ventricle, there acting as a guiding rail for the coaxial advancement of the delivery system catheters. Then, at a point external to the body, by inserting the guide wire 131 into the distal tip of the carrier catheter 220, the assembled delivery catheter system 200 with carrier catheter 220, delivery catheter 210 and sheath 101 is then advanced into the body coaxially over the guidewire 131 to a position proximate to but short of the target anatomic site—in this case, the diseased heart valve seat 141.

Figure 5C:
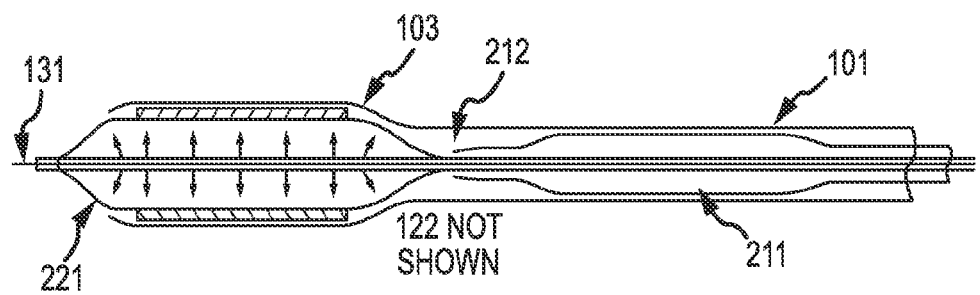
FIG. 5C is a side view of the system shown in FIG. 5B, wherein full inflation of the leading carrier balloon partially expands the stent-valve within an expandable sheath segment.

Referring now to FIG. 5C, in at least one embodiment, when in the aorta the carrier segment 221 is further expanded to effect expansion of the stent-valve 120 within the outer delivery sheath so that the delivery balloon can be advanced axially and positioned radially to the interior of the stent-valve 120. That is, when in the aorta, the leading carrier segment 221 is expanded, such as by balloon inflation, thus partially expanding the catheter-deliverable device (stent-valve 120) within the expandable distal segment 103 of the delivery sheath 101. In at least one embodiment, the outer delivery sheath 101 includes an expandable, flexible distal segment 103 that allows partial expansion of the stent-valve 120 within the outer delivery sheath, such as to a sufficient diameter to receive the unexpanded delivery balloon 211. Although the distal segment of the outer delivery sheath may be expandable, the outer delivery sheath shaft 104 located axially proximal to the carrier segment 221 preferably remains relatively small in diameter, that is, at its original unexpanded diameter, such as having a 14 French inside diameter at the entry point of the body and blood vessel.

Figure 5D:
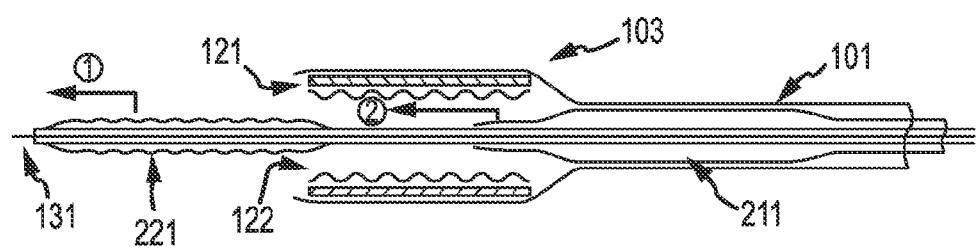
FIG. 5D is a side view of the system shown in FIG. 5C, wherein at "(1)" the leading carrier balloon is deflated and advanced out of the stent-valve, and wherein at "(2)" the delivery balloon is advanced into position within stent-valve to "dock" with or "capture" the stent-valve.

With reference now to FIG. 5D, after partial expansion of the stent-valve 120 within the distal portion 103 of the outer delivery sheath 101, the carrier segment 221 is contracted as by balloon deflation and is then advanced axially beyond the outer delivery sheath 101 and out of the catheter-deliverable device (stent-valve 120) leaving it retained within the expanded distal segment 103 of the sheath 101.

The delivery segment balloon 211 is then axially advanced to a position radially to the interior of the stent-valve 120. With the delivery segment 211 of the delivery catheter 210 then coaxially advanced over the shaft 224 of the carrier catheter to a position astride the catheter-deliverable device (stent-valve 120) within the delivery sheath 101, the delivery segment balloon 211 is then partially expanded to dock or capture the stent-valve 120.

Figure 5E:
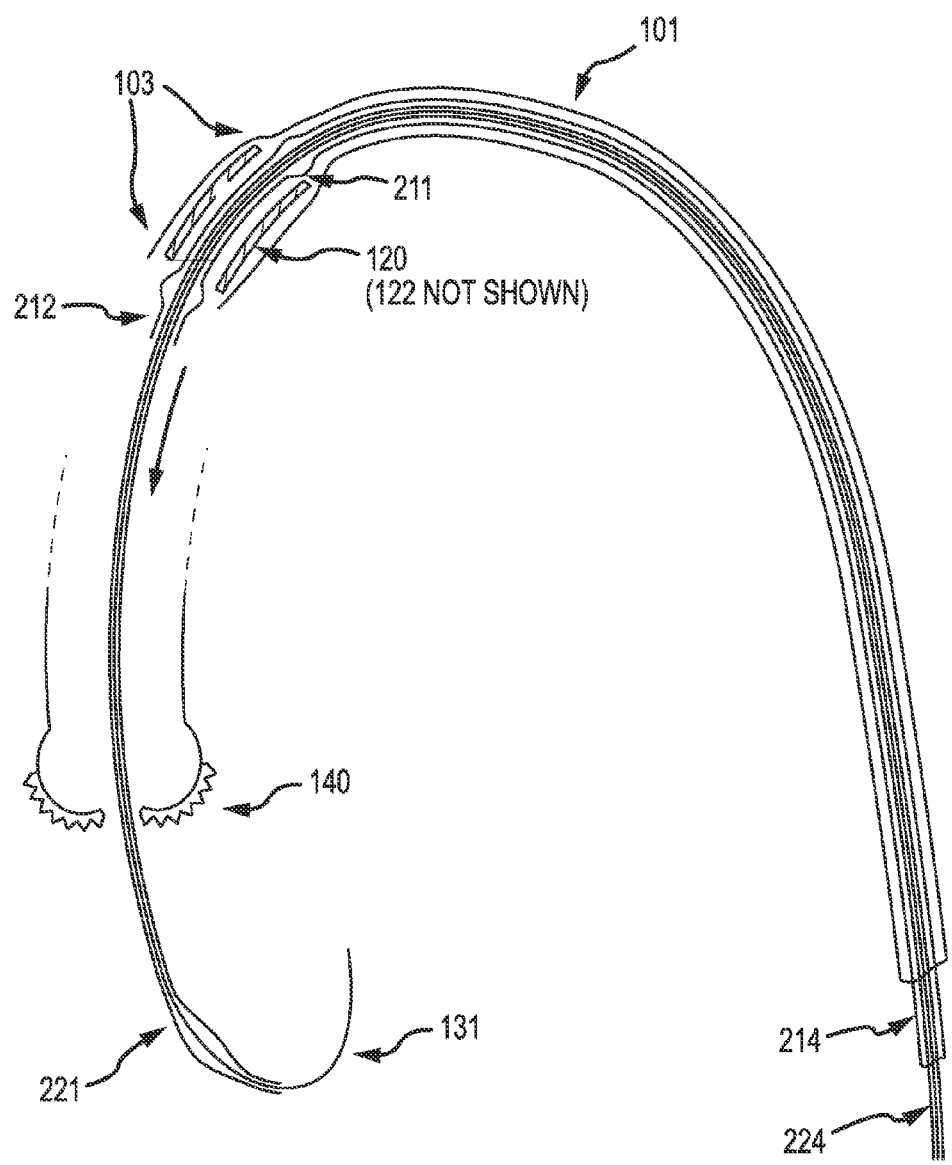
FIG. 5E is a side view of the system shown in FIG. 5D, wherein the leading carrier balloon and guidewire are first advanced into the left ventricle (in the case of implantation in the native aortic valve seat), and wherein the leading carrier balloon shaft then acts as a guide rail for delivery of the balloon catheter.

Referring now to FIG. 5E, the leading carrier segment balloon 221 of the carrier catheter 220 is then advanced across the target anatomic plane (native heart valve seat 141) coaxially following the guide wire 131 there in place, where it then provides additional mechanical guidance and support for the further coaxial advancement of the larger delivery catheter 210 upon the shaft 224 of the carrier catheter 220. Alternatively, the carrier catheter 220 may be coaxially withdrawn from the system and the body leaving the guide wire in place, then a shaped catheter (one with specifically designed terminal curves, such as "pig tail" or Amplatz type curves commonly found on angiographic catheters, to facilitate its being properly situated relative to the anatomy) may then be advanced over the guide wire to the upstream anatomic chamber, its shaft then substituting for the shaft 224 of the carrier catheter. Accordingly, FIG. 5E illustrates the guidewire 131 and carrier segment 221 as having passed the aortic valve such that the guidewire and carrier segment reside within the patient's left ventricle. Axial advancement of the carrier segment 221 and the carrier catheter shaft 224 can be done independent of the location of the delivery balloon 211. Thereafter, the delivery segment balloon 211 and the delivery catheter shaft 214 are axially advanced co-axially over the carrier catheter shaft 224 that acts as a guide rail for the delivery segment balloon 211. More particularly, with the projected tip 212 of the delivery catheter 211 leading beyond the tip of the sheath, the delivery segment 211, catheter-deliverable device (stent-valve 120), and delivery sheath 101 are advanced together as a unit across the target anatomic plane (native heart valve seat 141, for example) to a position astride the target plane deemed suitable for deployment of the catheter-deliverable device (stent-valve 120).

Once positioned at the plane of the valve seat of the patient's aortic valve, the delivery sheath 101 is coaxially retracted with the delivery catheter held in place so as to expose the catheter-deliverable device (stent-valve 120) retained upon the delivery segment 211 at the site of deployment. Thereafter, the final delivery balloon is expanded to deploy the stent-valve 120.

With full expansion and deployment of the catheter-deliverable device (stent-valve 120) the device is retained within the target anatomic plane (native heart valve seat 141). The delivery segment 211 is then contracted as by balloon deflation, function of the deployed device is confirmed, and the delivery catheter, carrier catheter, delivery sheath 101, and guide wire 131 are retracted from the anatomic target area and removed from the body to complete the procedure.

Expandable Outer Delivery Sheath

As described herein, at least one embodiment of the endoluminal delivery system includes an outer delivery sheath that further comprises a distal segment that is expandable. Several different ways of providing an expandable distal segment are described in the following paragraphs.

Figure 6A:
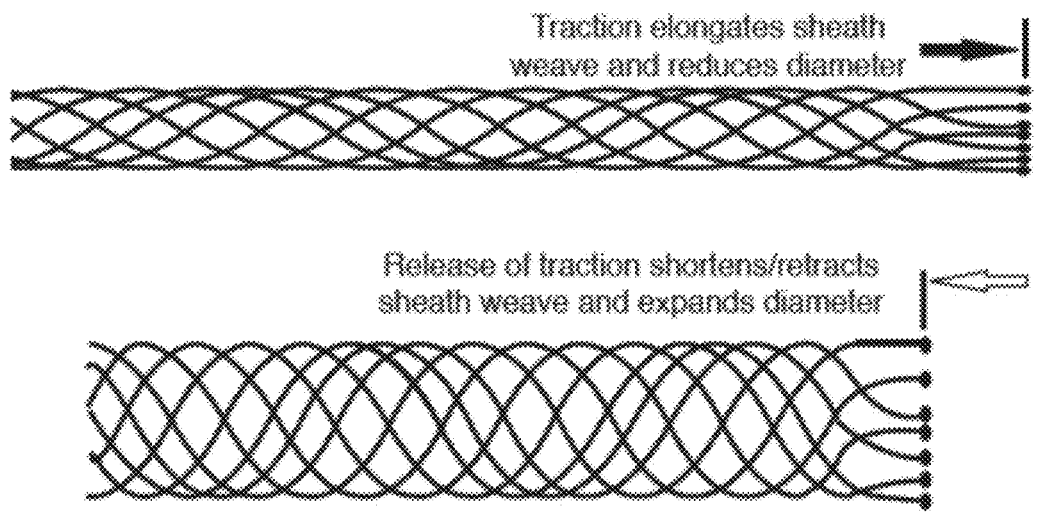
FIG. 6A is a side view of an embodiment of a sheath, wherein traction elongates the sheath weave and reduces its diameter, and wherein release of the traction shortens/retracts the sheath weave and expands its diameter.

Referring now to FIG. 6A, the distal segment of the outer delivery sheath 310 may comprise a woven alloy wire portion 311. By way of example and not limitation, the distal segment may be similar in design to the IDEV TECHNOLOGIES SUPERA® stent that includes woven nitinol wire. Alternatively, in at least one embodiment, the woven wire portion 311 may further comprise a flexible plastic investment; that is, a configuration wherein the woven wire portion resides within a flexible plastic matrix forming a tubular portion of the outer delivery sheath. In typical operation, the wire weave is formed in expanded configuration and elongated by longitudinal traction force on the wire elements with resulting contraction of the tubular form to a decreased diameter. Thereafter, the release of traction force effects self-expansion of the weave. In at least one embodiment, a distal portion of the distal segment of the outer delivery sheath 310 may be widened by using control lines to pull on control ends of the woven wire portion of the distal segment.

Figure 6B:
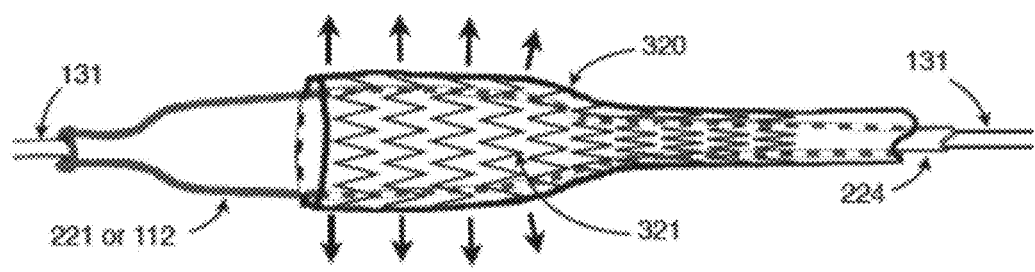
FIG. 6B is a side view of an embodiment of a cut shape memory alloy stent (nitinol) within a sheath wall investment that expands as a contained balloon and/or stent-valve (omitted for clarity) is expanded therein and self-contracts as the balloon is deflated.

Referring now to FIG. 6B, in an alternative embodiment, the distal segment of the outer delivery sheath 320 includes a cut nitinol stent 321 residing within the sheath investment. More particularly, the distal segment of the outer delivery sheath includes a nitinol stent 321 embedded within the distal segment, wherein the nitinol stent 321 provides shape-memory functionality for the distal segment. As a result, when the balloon catheter is inflated within the distal segment with the stent-valve 120 mounted on it, the distal segment expands to accommodate the inflated balloon catheter and stent-valve. Thereafter, when the balloon catheter is pushed out of the outer delivery sheath 320, the distal segment then retracts because of the shape-memory functionality associated with the nitinol stent 321 residing with the distal segment.

Figure 6C:
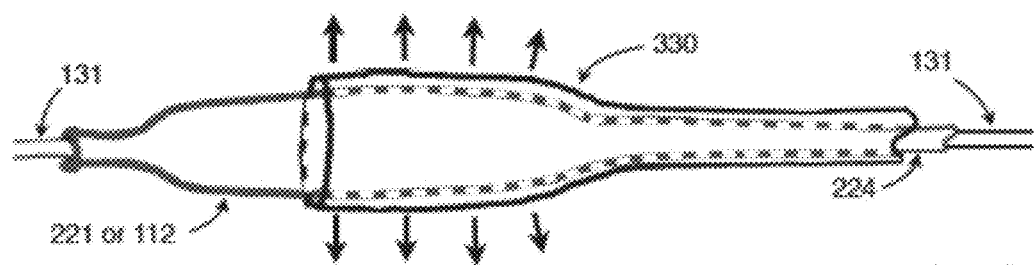
FIG. 6C is a side view of an embodiment of a plastic material sheath that passively expands.

Referring now to FIG. 6C, in at least one embodiment the distal segment of the outer delivery sheath 330 comprises an elastic material that can passively expand and optionally retract. That is, when a balloon catheter is expanded within the distal segment, the elastic material accommodates the expansion. Thereafter, with deflation of the balloon catheter the elastic material forming the distal segment retracts. Alternatively, the sheath material, such as PTFE (polytetrafluoroethylene) may expand but not contract. In such case, the thin-walled sheath material folds inward along longitudinal lines when retracted through a proximally disposed entry sheath or the vascular entry point itself, permitting ready removal from the body, even in a persistently expanded condition.

Figure 6D:
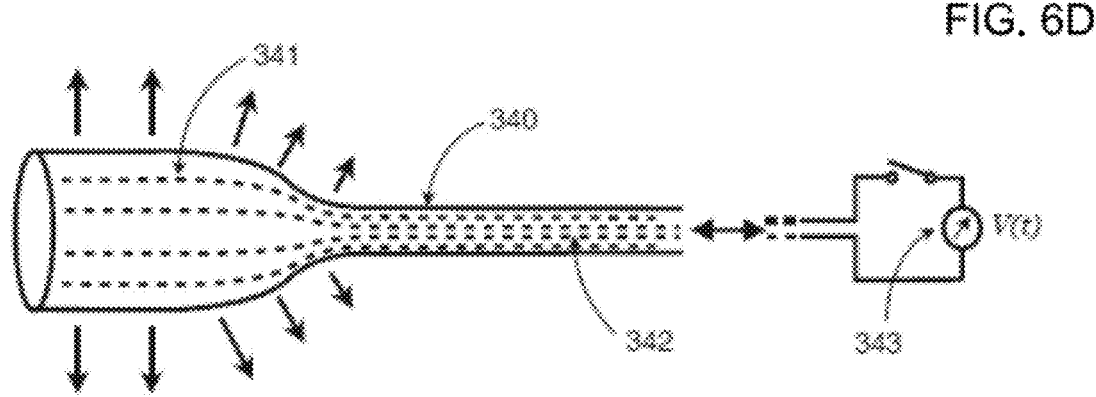
FIG. 6D is a side view of an embodiment of electrically actuated piezo-ceramic (p-c) elements sealed within an elastic sheath wall, wherein each p-c element is connected by a conductor pair to a voltage controlled power source, wherein a switch engages a power source, and wherein p-c elements expand the sheath when electrically energized.

Referring now to FIG. 6D, in an alternative embodiment, the distal segment of the outer delivery sheath 340 includes a plurality of electrically actuated piezo-ceramic elements 341. Electrical wiring or conductors 342 extend to the proximal end of the outer delivery sheath 340 to facilitate application of an electrical current to the piezo-ceramic elements 341. When desired, the surgeon closes a circuit to engage a power source 343 and apply the electrical current to the piezo-ceramic elements 341 via the electrical wiring or conductors 342. Upon being energized, the piezo-ceramic elements 341 expand the distal segment of the outer delivery sheath 340. Contraction of the distal segment is achieved by terminating the electrical current to the piezo-ceramic elements 341. Further reference here is made to U.S. Pat. No. 5,415,633, the content of which is incorporated by reference in its entirety.

Figure 6E:
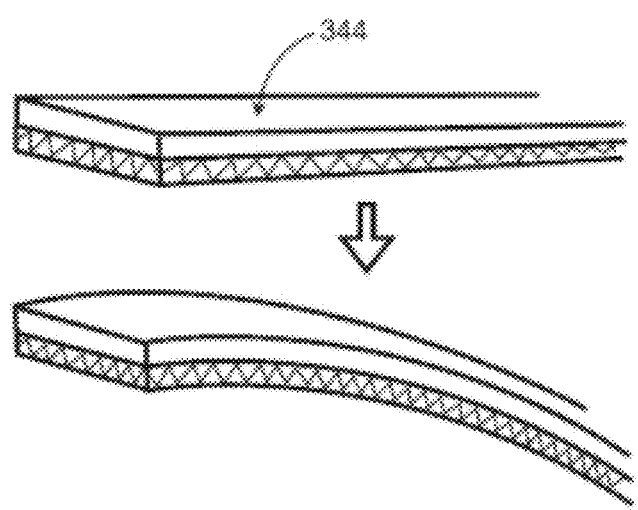
FIG. 6E is a perspective view of an embodiment of actuator elements that utilize differential alloy laminates, wherein an application of current induces bend in the actuator.

Referring now to FIG. 6E, a variation of the use of electrically charged elements comprises the use of active elements featuring differential alloy sandwiches or laminates 344 that bend when a current is applied. The bending of the active elements causes the distal segment to expand. As with the piezo-ceramic elements 341 described above, contraction of the distal segment is achieved by terminating the application of electrical current to the differential alloy sandwiches or laminates 344.

Figure 7:
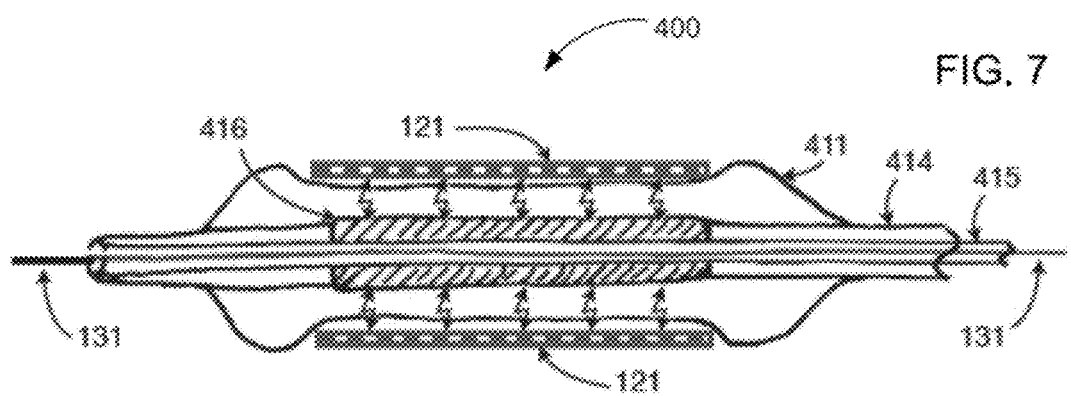
FIG. 7 is a side view of an embodiment of a device for retaining a stent-valve on a delivery balloon by magnetic or electromagnetic means (for FIGS. 7-8B, conductors and a power source for electromagnet are not shown; the valve membrane or other valve mechanism is not shown; the balloon inflation lumen and optional control lines/harness are omitted for clarity)

In another alternative embodiment, a magnetic or electromagnetic force is used to retain a stent-valve 120 on a delivery segment balloon for advancement to the target valve plane and subsequent deployment. More particularly, and with reference now to FIG. 7, an alternative endoluminal magnetic delivery system 400 is shown that utilizes a magnetic or electromagnetic force to maintain the position of the stent-valve 120 on the delivery segment balloon 411, wherein the delivery segment balloon 411 is located at or near the distal portion of a delivery catheter shaft 414. The magnet or electromagnet 416 are preferably incorporated into the balloon catheter shaft 414 co-axial to and axially centered along the delivery segment balloon 411 so as to align with the axial position of the mounted stent-valve. As one of skill in the art will appreciate, the stent-valve 120 must incorporate a material susceptible to magnetism in a sufficient quantity and distribution to facilitate attraction of the stent-valve 120 to the magnet or electromagnet 416 incorporated into the balloon catheter shaft 414. A guidewire 131 serves to guide the co-axially situated delivery balloon catheter 410. The delivery balloon may be partially expanded to: (a) provide a nose cone for facilitating insertion of the delivery system into, and traverse through the patient's blood vessel; and/or (b) to provide further frictional force for securing the stent-valve 120. Since the stent-valve 120 is held in place by a magnetic or electromagnetic force as well as any further frictional force due to partial expansion of the delivery balloon, the stent-valve 120 can be securely advanced through the patient's vascular system without need of an outer delivery sheath, thereby simplifying and reducing the profile of the delivery system. Once the target valve plane is reached, the delivery balloon 411 is expanded, thereby overcoming the magnetic or electromagnetic force (of course, an electromagnetic force may be terminated by stopping current to the electromagnet), to deploy the stent-valve 120 at the plane of the diseased native valve. Similarly, the magnet of the magnetic delivery catheter 410 may be incorporated into the delivery segment balloons of the in-line dual balloon system 100 and/or the telescoping catheter delivery system 200 in a similar manner to facilitate capture and retention of the stent-valve upon the delivery segment balloon in its traverse through the anatomic structures.

Figure 8A:
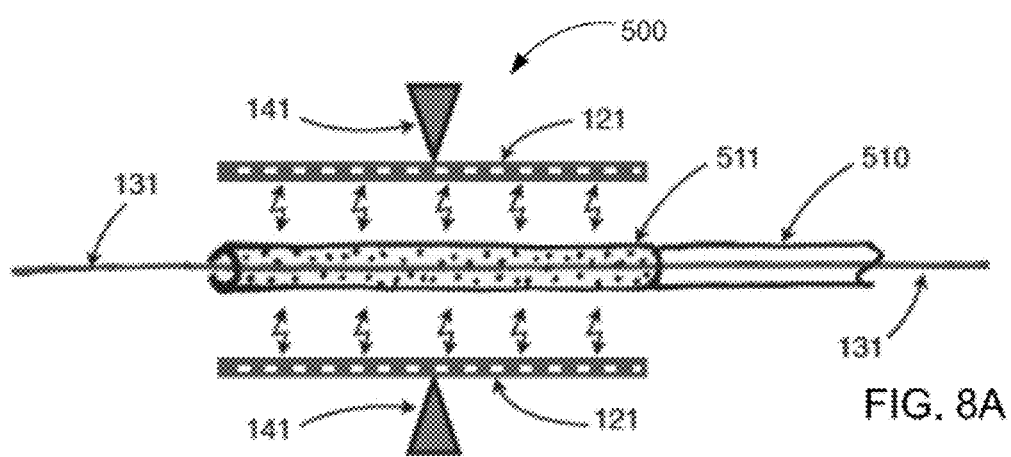
FIG. 8A is a side view of an embodiment of a retrieval catheter device that utilizes magnetic force to retrieve a stent-valve.
Figure 8B:
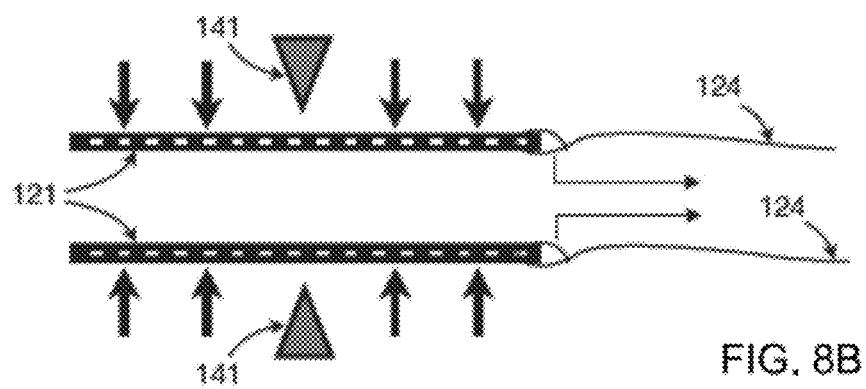
FIG. 8B is a side view of a stent-valve wherein the stent-valve is contracted by magnetic force and thereafter can be retracted from the native valve seat by optional control lines or a harness.

In addition to endoluminal delivery of a stent-valve 120, at least one embodiment of the one or more present inventions is directed to a retrieval and/or repositioning system 500 that can be used to remove a deployed stent-valve 120 from a patient, or otherwise reposition the stent-valve 120 within the patient. With reference now to FIGS. 8A and 8B, an embodiment of a retrieval and/or repositioning system 500 is shown. The retrieval and/or repositioning system comprises a retrieval catheter 510 on a distal portion of which is integrated a magnet 511, and more preferably, an electromagnet of sufficient strength to at least partially collapse and secure a previously deployed stent-valve 120. With reference to FIG. 8B, the partially collapsed valve is then either withdrawn (that is, retrieved from the patient), for example as by traction on optional control lines 124 as shown, or repositioned and then redeployed.

Figure 8C:
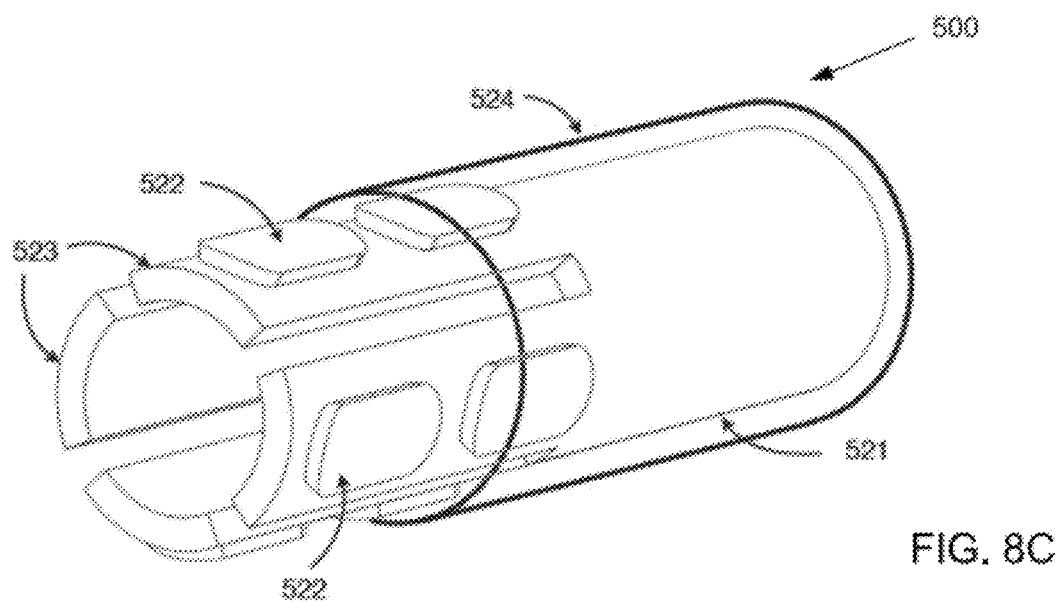
FIG. 8C is a side perspective view of an embodiment of a multipolar magnetic retrieval catheter system.
Figure 8D:
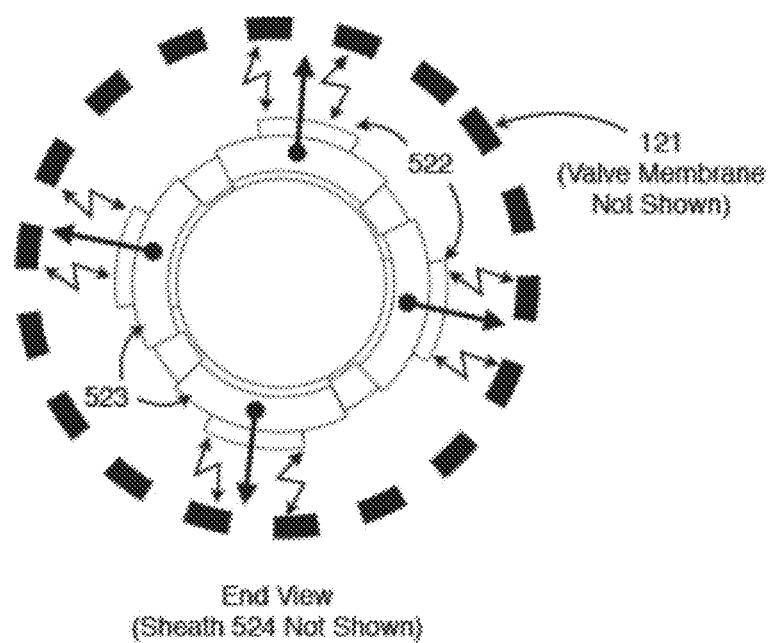
FIG. 8D is an end view of the system shown in FIG. 8C positioned radially within a stent-valve.

Referring now to FIGS. 8C and 8D, in a separate embodiment, a multipolar magnetic retrieval catheter system 520 is provided in which multiple magnetic elements 522 are circumferentially arrayed and disposed at a distal portion of a retrieval catheter 521 in a manner that allows the radially outward movement of the magnets 522, and the portions of the underlying catheter elements 523 to which they are attached, into contact with the radially interior surface of the deployed stent-valve 120. In at least one embodiment, the underlying portions 523 of the catheter to which the magnets 522 are attached are longitudinally separate from each other so that they are free to move independently from each other as the attached magnets 522 move radially outward. In at least one embodiment, the magnets 522 are of like polarity and are initially restrained into proximity with each other by an overlying sheath mechanism. When said sheath 524 is retracted the distal catheter portions 523 with their attached magnets 522 move radially outward under repulsive magnetic force into contact with the stent-valve 120. The close proximity if not complete contact of the magnets 522 to the stent-valve frame 121 advantageously maximizes the retention force facilitating the traction force applied in the removal of the device from the valve plane. The sheath 524 may be re-advanced over the magnetic distal portions 523 of the catheter, thus applying radially inward force on the device frame that serves to contract it and facilitate its removal under axial traction.

Shaped Catheter

The various sheath and catheter shafts described herein for the various embodiments may include a "shaped" distal portion. More particularly, a "shaped" catheter may be used to assist in crossing anatomic resistance or provide guidance for recrossing the valve plane in the event the guide wire is displaced from the ventricle. This problem occurs when the stent-valve and the delivery system are advanced around the aorta. In such a situation, the traction forces, not uncommonly, will pull the guide wire out of the ventricle. If this happens—with the delivery system already in the aorta—it requires the delivery system be removed from the patient's body and the sequence started over from the beginning. Advantageously, one or more embodiments described herein can assist with avoiding this problem. That is, a catheter can be used that includes a distal portion with one or more curved shapes, such as "pig tail" or Amplatz type curves commonly found on angiographic catheters, and including a central coaxial lumen through which is passed the guidewire. The shaped catheter is used to "steer" the guide wire across the very narrowed valve orifice. Thus, in one embodiment, a "shaped" catheter is passed within the central lumen of the delivery catheter. In such a configuration, the guide wire can be re-crossed through the valve plane more readily, and the shaped catheter—advantageously, a relatively firm catheter—can be advanced to the ventricle and left to act as an enhanced support rail for the delivery catheter.

To assist in the understanding of the present invention the following list of components and associated numbering found in the drawings is provided herein:

| Number | Component |
|---|---|
| 100 | In-Line Dual Balloon Catheter Delivery System |
| 101 | Delivery Sheath |
| 102 | Optional Flange Of Internal Sheath |
| 103 | Expandable, Flexible Sheath Segment |
| 104 | Sheath Body |
| 110 | Dual In-Line Balloon Catheter Assembly |
| 111 | Delivery Segment Is Delivery Balloon |
| 112 | Carrier Segment Is In-Line Leading Carrier Balloon |
| 113 | Optional Nose Cone |
| 114 | Exit Of Distal Control Lines From Catheter Shaft |
| 120 | Stent-Valve Assembly |
| 121 | Valve Frame |
| 122 | Collapsed Valve Membrane |
| 123 | Optional Control Lines Attached To Distal End Of Valve Frame (Passed Within Catheter Shaft) |
| 124 | Optional Control Lines Attached To Proximal End Of Valve Frame |
| 130 | Guide Wire Assembly |
| 131 | Guide Wire |
| 140 | Native Heart Valve |
| 141 | Native Heart Valve Seat |

-continued

| Number | Component |
|---|---|
| 200 | Telescoping Balloon Catheter Delivery System |
| 210 | Delivery Balloon Catheter Assembly |
| 211 | Delivery Segment Is Delivery Balloon |
| 212 | Tip Of Delivery Segment Balloon |
| 213 | Partially Inflated Leading Tip Of Delivery Segment Balloon |
| 214 | Delivery Balloon Catheter Shaft |
| 220 | Carrier Balloon Catheter Assembly |
| 221 | Carrier Segment Is Leading Balloon That Coaxially Telescopes Within Central Lumen Of Delivery Segment Balloon |
| 222 | Tip Of Carrier Segment Balloon |
| 223 | Inflated Leading Tip Of Carrier Segment Balloon |
| 224 | Shaft Of Carrier Catheter |
| 300 | Expandable Sheath System |
| 310 | Woven Wire Sheath |
| 320 | Sheath With Embedded Nitinol Stent |
| 321 | Nitinol Stent |
| 330 | Flexible Plastic Sheath |
| 340 | Electronically Actuated Sheath |
| 341 | Piezo-Ceramic Elements |
| 342 | Conductors |
| 343 | Power Source |
| 344 | Alloy Laminates |
| 400 | Magnetic Balloon Catheter Delivery System |
| 410 | Magnetic Balloon Delivery Catheter |
| 411 | Delivery Balloon |
| 412 | Tip Of Magnetic Balloon Delivery Catheter |
| 413 | Partially Inflated Tip Of Delivery Balloon |
| 414 | Shaft Of Magnetic Balloon Delivery Catheter |
| 415 | Guide Wire Lumen Of Magnetic Balloon Delivery Catheter |
| 416 | Magnet Or Electromagnet |
| 500 | Magnetic Retrieval Catheter System |
| 510 | Magnetic Retrieval Catheter Assembly |
| 511 | Magnet Or Electromagnet |
| 520 | Multipolar Magnetic Retrieval Catheter Assembly |
| 521 | Multipolar Magnetic Retrieval Catheter |
| 522 | Magnets-Circumferentially Arrayed |
| 523 | Distal Mobile Catheter Elements Attaching To Magnets |
| 524 | Sheath |

The one or more present inventions may be embodied in other specific forms without departing from its spirit or essential characteristics. The described embodiments are to be considered in all respects only as illustrative and not restrictive. The scope of the one or more present inventions is, therefore, indicated by the appended claims rather than by the foregoing description. All changes which come within the meaning and range of equivalency of the claims are to be embraced within their scope.

The one or more present inventions, in various embodiments, includes components, methods, processes, systems and apparatus substantially as depicted and described herein, including various embodiments, subcombinations, and subsets thereof. Those of skill in the art will understand how to make and use the one or more present inventions after understanding the present disclosure.

The one or more present inventions, in various embodiments, includes providing devices and processes in the absence of items not depicted and/or described herein or in various embodiments hereof, including in the absence of such items as may have been used in previous devices or processes (e.g., for improving performance, achieving ease and/or reducing cost of implementation).

The foregoing discussion of the one or more present inventions has been presented for purposes of illustration and description. The foregoing is not intended to limit the one or more present inventions to the form or forms disclosed herein. In the foregoing Detailed Description for example, various features of the one or more present inventions are grouped together in one or more embodiments for the purpose of streamlining the disclosure. This method of disclosure is not to be interpreted as reflecting an intention that the claimed one or more present inventions requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the one or more present inventions.

Moreover, though the description of the one or more present inventions has included description of one or more embodiments and certain variations and modifications, other variations and modifications are within the scope of the one or more present inventions (e.g., as may be within the skill and knowledge of those in the art, after understanding the present disclosure). It will be understood that many changes in the details, materials, steps and arrangements of elements, which have been herein described and illustrated in order to explain the nature of the invention, may be made by those skilled in the art without departing from the scope of embodiments of the one or more present inventions. It is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter.

What is claimed is:

1. A system for treating a native heart valve in a patient using endoluminal delivery through vasculature of a patient to a native heart valve seat, the system comprising:
   a stent-valve;
   an outer delivery sheath including a distal section, wherein at least a portion of the outer delivery sheath is sized for insertion into the vasculature of the patient, wherein at least a portion of the distal section of the outer delivery sheath is expandable and comprises a plurality of piezo-ceramic elements configured to expand the distal section of the outer delivery sheath upon electrically activating the plurality of piezo-ceramic elements;
   a carrier segment located at a distal portion of a catheter shaft, the carrier segment having an outer surface sized to temporarily hold the stent-valve in the distal section of the outer delivery sheath, wherein at least a portion of the catheter shaft is located within and coaxial to the outer delivery sheath; and
   a delivery segment located coaxially to the outer delivery sheath, the delivery segment having an outer surface sized to radially fit within the stent-valve after detaching the stent-valve from the carrier segment when the stent-valve resides within the distal section of the outer delivery sheath, wherein the delivery segment is configured to deploy the stent-valve at the location of the native heart valve seat.

2. The system of claim 1, wherein the distal section includes at least one of an internal projection and a narrowed area extending radially inward from an interior surface of the distal section.

3. The system of claim 1, wherein a portion of an internal surface of the outer delivery sheath further comprises a guide for retaining at least a portion of a longitudinally extending element configured to selectively manipulate at least a part of the outer delivery sheath or a structure coaxial to the outer delivery sheath.

4. The system of claim 1, wherein a portion of an internal surface of the outer delivery sheath further comprises a guide, the guide comprising at least one of:

(a) a lumen; and
(b) a grommet;
wherein the guide retains at least one control line for selective retention of the stent-valve.

5. The system of claim 1, wherein the carrier segment is situated upon the catheter shaft, and wherein the delivery segment is associated with a delivery segment shaft that is coaxial to the catheter shaft and axially moveable relative to the catheter shaft.

6. The system of claim 1, wherein the carrier segment is an expandable balloon having an expanded diameter smaller than an expanded diameter for the delivery segment.

7. The system of claim 1, wherein the delivery segment is an expandable balloon having an expanded diameter larger than an expanded diameter for the carrier segment.

8. The system of claim 1, wherein at least one of the carrier segment and the delivery segment is a mandrel.

9. The system of claim 1, wherein the mandrel is expandable by mechanical or electromechanical means.

10. The system of claim 1, wherein the delivery segment is located axially proximal to the carrier segment.

11. The system of claim 1, wherein the delivery segment includes a magnet to aid in capture and retention of the stent-valve on the delivery segment.

* * * * *